(12) United States Patent
Stahl et al.

(10) Patent No.: US 11,930,838 B2
(45) Date of Patent: Mar. 19, 2024

(54) POUCHED PRODUCT WITH LIQUID FLAVOR COMPOSITION

(71) Applicant: PHILIP MORRIS PRODUCTS S.A., Neuchatel (CH)

(72) Inventors: My Ly Lao Stahl, Vejle Ost (DK); Heidi Ziegler Bruun, Vejle Ost (DK); Bruno Provstgaard Nielsen, Vejle Ost (DK); Jesper Neergaard, Aabenraa (DK); Bine Hare Jakobsen, Ry (DK)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 0 days.

(21) Appl. No.: 17/422,684

(22) PCT Filed: Jun. 5, 2020

(86) PCT No.: PCT/DK2020/050162
§ 371 (c)(1),
(2) Date: Jul. 13, 2021

(87) PCT Pub. No.: WO2020/244724
PCT Pub. Date: Dec. 10, 2020

(65) Prior Publication Data
US 2022/0039455 A1 Feb. 10, 2022

(30) Foreign Application Priority Data

Jun. 7, 2019 (DK) .................................. 2019 00698
Sep. 30, 2019 (DK) .................................. 2019 70610
Sep. 30, 2019 (DK) .................................. 2019 70611
Sep. 30, 2019 (DK) .................................. 2019 70612

(51) Int. Cl.
| | |
|---|---|
| A24B 15/16 | (2020.01) |
| A24B 13/00 | (2006.01) |
| A24B 15/24 | (2006.01) |
| A24B 15/30 | (2006.01) |
| A24B 15/32 | (2006.01) |
| A24B 15/38 | (2006.01) |
| A24B 15/40 | (2006.01) |
| A24B 15/42 | (2006.01) |
| A61K 9/00 | (2006.01) |
| A61K 31/465 | (2006.01) |

(52) U.S. Cl.
CPC .............. *A24B 15/16* (2013.01); *A24B 13/00* (2013.01); *A24B 15/243* (2013.01); *A24B 15/302* (2013.01); *A24B 15/303* (2013.01); *A24B 15/32* (2013.01); *A24B 15/385* (2013.01); *A24B 15/403* (2013.01); *A24B 15/42* (2013.01); *A61K 9/006* (2013.01); *A61K 9/009* (2013.01); *A61K 31/465* (2013.01)

(58) Field of Classification Search
CPC ......... A24B 13/00; A24B 15/16; A24B 15/18; A24B 15/302; A24B 15/32; A24B 15/403; A24B 15/42; A61K 9/009; A61K 31/465

USPC .......................................... 131/369, 352, 347
See application file for complete search history.

(56) References Cited

U.S. PATENT DOCUMENTS

| | | | |
|---|---|---|---|
| 5,167,244 A | 12/1992 | Kjerstad | |
| 8,863,755 B2 | 10/2014 | Zhuang et al. | |
| 9,402,809 B2 | 8/2016 | Axelsson et al. | |
| 11,096,412 B2* | 8/2021 | Stahl et al. | ............ A61K 9/146 |
| 11,399,562 B2* | 8/2022 | Stahl | ..................... A24B 15/42 |
| 11,540,557 B2* | 1/2023 | Stahl et al. | ............ A24B 15/14 |
| 2005/0034738 A1 | 2/2005 | Whalen | |
| 2005/0053665 A1 | 3/2005 | Ek et al. | |
| 2010/0282267 A1* | 11/2010 | Atchley | ............... A24B 15/186 |
| | | | 131/274 |
| 2011/0214681 A1 | 9/2011 | Axelsson et al. | |
| 2012/0247492 A1 | 10/2012 | Kobal et al. | |
| 2013/0108558 A1 | 5/2013 | Andersen | |
| 2013/0152953 A1 | 6/2013 | Mua et al. | |
| 2015/0020818 A1 | 1/2015 | Gao et al. | |
| 2015/0068545 A1 | 3/2015 | Moldoveanu et al. | |
| 2015/0096576 A1 | 4/2015 | Gao et al. | |
| 2016/0000140 A1 | 1/2016 | Sebastian et al. | |
| 2016/0192703 A1 | 7/2016 | Sebastian et al. | |
| 2017/0318858 A1 | 11/2017 | Hodin et al. | |
| 2018/0271139 A1 | 9/2018 | Aspgren et al. | |

(Continued)

FOREIGN PATENT DOCUMENTS

| | | |
|---|---|---|
| CN | 103491958 A | 1/2014 |
| CN | 103494324 A | 1/2014 |
| CN | 107205471 A | 9/2017 |

(Continued)

OTHER PUBLICATIONS

Seidenberg, Andrew B., Olalekan A. Ayo-Yusuf and Vaughan W. Rees. Characteristics of "American Snus" and Swedish Snus Products for Sale in Massachusetts, USA. Nicotine & Tobacco Research, vol. 20, No. 2, 2018, 262-266.

(Continued)

*Primary Examiner* — Dionne W. Mayes

(74) *Attorney, Agent, or Firm* — Oblon, McClelland, Maier & Neustadt, L.L.P.

(57) ABSTRACT

An oral pouched product is disclosed, the pouched product comprising a saliva permeable pouch and a pouch composition, the pouch composition comprising a powdered composition, water, and a liquid flavor composition, wherein the liquid flavor composition is added to the powdered composition after the water. A further oral pouched product and a method of manufacturing an oral pouched product is disclosed.

14 Claims, No Drawings

(56) References Cited

U.S. PATENT DOCUMENTS

| | | |
|---|---|---|
| 2019/0037909 A1 | 2/2019 | Greenbaum et al. |
| 2020/0297024 A1 | 9/2020 | Bodin |

FOREIGN PATENT DOCUMENTS

| | | | |
|---|---|---|---|
| CN | 107319629 A | | 11/2017 |
| EP | 2692254 A1 | | 2/2014 |
| EP | 3087852 A1 | | 11/2016 |
| EP | 3491940 A1 | | 6/2019 |
| GB | 673587 A | | 6/1952 |
| NO | 20170683 A1 | | 10/2018 |
| RU | 2 608 902 | | 5/2015 |
| RU | 2 617 262 | | 3/2016 |
| WO | 2007084587 A2 | | 7/2007 |
| WO | 2007104573 A2 | | 9/2007 |
| WO | 2008056135 A2 | | 5/2008 |
| WO | 2008152469 A2 | | 12/2008 |
| WO | 2009010881 A2 | | 1/2009 |
| WO | 2010121619 A1 | | 10/2010 |
| WO | 2012134380 A1 | | 10/2012 |
| WO | 2013090366 A2 | | 6/2013 |
| WO | 2013152918 A1 | | 10/2013 |
| WO | 2015052282 A1 | | 4/2015 |
| WO | 2015067372 A1 | | 5/2015 |
| WO | 2015193379 A1 | | 12/2015 |
| WO | 2016083463 A1 | | 6/2016 |
| WO | WO 2016/090075 A1 | | 6/2016 |
| WO | 2017153718 A1 | | 9/2017 |
| WO | 2018011470 A1 | | 1/2018 |
| WO | 2018126262 A2 | | 7/2018 |
| WO | 2018197454 A1 | | 11/2018 |
| WO | 2018233795 A1 | | 12/2018 |
| WO | 2019115778 A1 | | 6/2019 |
| WO | 2020157280 A1 | | 8/2020 |

OTHER PUBLICATIONS

Wikipedia, "Sugar alcohol", https://en.wikipedia.org/wiki/Sugar_alcohol; downloaded from Internet on Sep. 27, 2017.

Combined Chinese Office Action and Search Report dated Aug. 3, 2022, in corresponding Chinese Patent Application No. 2020800415268 (with English Translation), 23 pages.

Office Action dated Oct. 9, 2023, in corresponding Russian Patent Application No. 2021139808 (with English-language Translation).

Search Report dated Oct. 9, 2023, in corresponding Russian Patent Application No. 2021139808 (with English-language Translation).

* cited by examiner

POUCHED PRODUCT WITH LIQUID FLAVOR COMPOSITION

FIELD OF THE INVENTION

The invention relates to an oral pouched product having a liquid flavor composition and a method of manufacturing such an oral pouched product.

BACKGROUND OF THE INVENTION

Delivery of nicotine by smoking has many well-known drawbacks, particular health related problem, such as inclusion of carcinogenic substances.

However, tobacco substitutes also suffer from disadvantages, such as inadequate relief of cravings for the user.

It is an object of one embodiment of the present invention to provide a nicotine containing pouch, e.g. as a tobacco substitute, which may solve the above problems.

Pouched products for oral delivery of e.g. nicotine are attractive for certain types of substance deliveries, such as active ingredients, sugar or sweeteners, etc. has proven to be a user friendly and attractive vehicle. A challenge in relation to such vehicles is however that the substance to be delivered must be released from the pouch at least partially as a result of salivation in the user's mouth. If such salivation is somehow counteracted or reduced, the intended deliver profile may be modified unintentionally. If releasing e.g. nicotine, dry-out of the pouch content may affect the contacting region(s) of the oral cavity.

The above challenge will be addressed in some aspects of the invention.

SUMMARY OF THE INVENTION

The invention relates in a first aspect to an oral pouched product comprising
  a saliva permeable pouch and a pouch composition,
  the pouch composition comprising
  a powdered composition,
  water, and
  a liquid flavor composition,
  wherein the liquid flavor composition is added to the powdered composition after the water.

An advantage of the present invention may be that a very desirable flavor release may be obtained. By using a liquid flavor composition according to the invention, the user experiences an initial, significant flavor burst. The liquid flavor composition is distributed over a large surface of the provided mixture comprising sugar alcohol and water and thereby facilitates an effective contact with saliva, which again advantageously promotes release of the flavor.

The invention counteracts drying out of the mucosa in other to stimulate salivation, in particular in the initial phase of the use of the pouch. The invention provides an initial flavor burst, which again facilitates salivation affecting both the release and at the same time makes it possible to obtain an impressive flavor profile, which is perceived very well by users in practice.

In a further aspect it is further noted that a synergy between the use of liquid flavor and water (moist in the pouch results) takes the taste perception to a new level, while at the same time affecting and dissolving sweeteners, e.g. sugar alcohols, and thereby providing further salivation.

The instant and effective contact of the liquid flavor with saliva could facilitate an increased salivation. This increased salivation could facilitate a faster moisturization of the pouch, thereby giving the user an improved moisture sensation of the pouch.

Also, this increased salivation could increase the dissolution of saliva-soluble components, such as sugar alcohols or an optional active ingredient, to give the user a higher initial sweetness sensation.

A significant advantage of the invention is that no drying of the composition is needed after adding the liquid flavor composition. Thus, the liquid flavor composition is added after adding the water.

In an advantageous embodiment of the invention, the pouch composition further comprises a powdered flavor composition.

By combining a liquid flavor composition with a powdered flavor composition according to the invention, the user experiences both an initial, significant flavor burst and a sustained release of flavor.

The liquid flavor is distributed over a large surface of the provided powdered mixture, e.g. comprising sugar alcohol and water and thereby facilitates an effective contact with saliva, which again advantageously promotes release of the flavor. At the same time, the powdered flavor composition facilitates a flavor release over a longer period, i.e. a sustained release of flavor.

The powdered flavor composition refers to a flavor composition that is provided as a solid or included in a solid matrix. A powdered flavor composition may be obtained by adding a liquid flavor to a solid matrix composition, such as e.g. a sugar alcohol to obtain a solid, powdered flavor composition. The powdered flavor material may be obtained e.g. by a spray drying process.

Thus, according to the invention, the liquid flavor composition is added to the powdered composition after the water, i.e. the water is added to the powdered composition, after which the liquid flavor composition is added to the resulting mixture of powdered composition and water.

In an advantageous embodiment of the invention, the pouch composition comprises the powdered flavor composition in an amount of at least 1% by weight of the pouch composition, such as at least 3% by weight of the pouch composition, such as at least 5% by weight of the pouch composition.

In an advantageous embodiment of the invention, the pouch composition comprises the powdered flavor composition in an amount of 1 to 20% by weight of the pouch composition, such as 3 to 15% by weight of the pouch composition, such as 5 to 10% by weight of the pouch composition.

In an alternative embodiment of the invention, the pouch composition is free of powdered flavor composition.

In an advantageous embodiment of the invention, the pouch composition comprises the liquid flavor composition in an amount of at least 0.01% by weight of the pouch composition, such as at least 0.1% by weight of the pouch composition, such as at least 0.5% by weight of the pouch composition.

In an advantageous embodiment of the invention, the pouch composition comprises the liquid flavor composition in an amount of 0.01 to 10% by weight of the pouch composition, such as 0.1 to 5% by weight of the pouch composition, such as 0.5 to 3% by weight of the pouch composition.

In an embodiment of the invention, the powdered and/or liquid flavor composition comprises at least one flavor compound selected from the group of coconut, coffee, chocolate, vanilla, citrus such as grape fruit, orange, lime, lemon, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, lemongrass, lime, jalapenos, chili (capsaicin), citrus, tobacco flavor, plum essence, blackcurrant, and any combination thereof.

The essential oils include peppermint, spearmint, menthol, eucalyptus, clove oil, bay oil, anise, thyme, cedar leaf oil, nutmeg, and oils of the fruits mentioned above. Essential oils may be used as liquid flavor composition, optionally with a liquid carrier added. In order to use essential oils as the powdered flavor composition, the essential oil would have to be added to a powdered carrier, e.g. granulated with a sugar alcohol or a water-soluble fiber.

In an advantageous embodiment of the invention, the pouch composition comprises a powdered flavor composition.

In an embodiment, the pouch composition is a mixture comprising sugar alcohol, water and the powdered flavor composition.

In an advantageous embodiment of the invention, the powdered flavor composition comprises a water-soluble carrier.

In an alternative embodiment, the powdered flavor composition comprises a water-insoluble carrier.

In an embodiment of the invention, the water-soluble carrier comprises or is sugar alcohol, maltodextrin, gum arabic (acacia), or any combination thereof.

In an advantageous embodiment of the invention, the powdered flavor composition comprises flavor compound in an amount of 10-95% by weight of the powdered flavor composition.

In example embodiments, the powdered flavor composition may have a loading (i.e. concentration of flavor compound) of at least 10%, such as between 15 and 30%, e.g. 20-25%. For some flavor compounds, such as e.g. menthol, a significantly higher loading may be used, such as e.g. around 80 or 95%.

In an advantageous embodiment of the invention, the powdered flavor provides flavor compound in an amount of 0.1 to 18% by weight of the pouch composition, such as 0.3 to 14% by weight of the pouch composition, such as 0.5 to 9% by weight of the pouch composition.

In an advantageous embodiment of the invention, the liquid flavor composition comprises a liquid carrier.

In an embodiment of the invention, the liquid carrier is an oil or a solvent. In an embodiment, the liquid carrier is selected from triacetin, propylene glycol, ethanol, medium chain triglycerides (MCT), and any combination thereof. Medium chain triglycerides (MCT) is e.g. known under the trade name MIGLYOL, In an advantageous embodiment of the invention, the liquid flavor composition comprises flavor compound in an amount of 10-100% by weight of the liquid flavor composition.

In an alternative embodiment, the liquid flavor composition comprises flavor compound in an amount below 10% by weight of the liquid flavor composition, such as in an amount of 0.1 to 10% by weight of the liquid flavor composition.

In an advantageous embodiment of the invention, the liquid flavor provides flavor compound in an amount of 0.01 to 5% by weight of the pouch composition, such as 0.03 to 4% by weight of the pouch composition, such as 0.05 to 3% by weight of the pouch composition.

In an advantageous embodiment of the invention, the liquid flavor composition comprises at least one of mint, eucalyptus, citrus such as lemon, lime, orange, or bergamot, liquorice, raspberry, blackcurrant or any combination thereof.

In an advantageous embodiment of the invention, the powdered composition comprises at least one sugar alcohol.

In an embodiment, xylitol, maltitol, mannitol, erythritol, isomalt, sorbitol, lactitol, and mixtures thereof may be used as the sugar alcohol. The at least one sugar alcohol may also comprise further sugar alcohols. As an example embodiment, hydrogenated starch hydrolysates may be used, which comprises a mixture of sorbitol, maltitol and further sugar alcohols.

In an advantageous embodiment of the invention, the at least one sugar alcohol is selected from xylitol, maltitol, mannitol, erythritol, isomalt, sorbitol, lactitol, and mixtures thereof.

In an advantageous embodiment of the invention, the at least one sugar alcohol is selected from xylitol, maltitol, mannitol, erythritol, isomalt, lactitol, and mixtures thereof.

In an embodiment of the invention, the at least one sugar alcohol comprises xylitol and/or erythritol.

In an advantageous embodiment of the invention, the pouch composition comprises at least two sugar alcohols.

In an embodiment of the invention, the at least two sugar alcohols are selected from xylitol, maltitol, mannitol, erythritol, and isomalt.

In an advantageous embodiment of the invention, the pouch composition comprises the at least one sugar alcohol in an amount of at least 1% by weight of the composition, such as at least 2% by weight of the composition, such as at least 5% by weight of the composition, such as at least 10% by weight of the composition.

In an advantageous embodiment of the invention, the pouch composition comprises the at least one sugar alcohol in an amount of 1 to 80% by weight of the composition, such as 2 to 70% by weight of the composition, such as 5 to 60% by weight of the composition, such as 10 to 50% by weight of the composition.

In an embodiment of the invention the pouch composition comprises the at least one sugar alcohol in an amount of 5 to 40% by weight of the composition, such as 5-30% by weight of the composition.

In an advantageous embodiment of the invention, the at least one sugar alcohol comprises a DC (direct compressible) grade sugar alcohol.

In an advantageous embodiment of the invention, at least 50% by weight of the at least one sugar alcohol is a DC (direct compressible) grade sugar alcohol.

In an embodiment of the invention, the at least one sugar alcohol comprises DC (direct compressible) grade sugar alcohol in an amount of 50-100% by weight of the at least one sugar alcohol, such as 60-80% by weight of the at least one sugar alcohol.

In an embodiment of the invention the at least one sugar alcohol comprises a non-DC (non-direct compressible) grade sugar alcohol.

In an advantageous embodiment of the invention, the powdered composition comprises water-insoluble fiber.

In an advantageous embodiment of the invention, the powdered composition comprises sugar alcohol and water-insoluble fiber.

An advantage of using a combination of sugar alcohols, water and water-insoluble fiber is that a very attractive soft, moist and moldable texture and mouthfeel is obtained. The desirable texture and mouthfeel may be obtained while still being able to store manufactured pouches together in abutment e.g. in cans etc. without sticking too much together to result in ruptures of the pouches when being removed.

In an advantageous embodiment of the invention, the water-insoluble fiber is a plant fiber.

In an advantageous embodiment of the invention, the water-insoluble fiber is selected from wheat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, cellulose fibers, powdered cellulose, bran fibers, bamboo fibers, and any combination thereof.

Powdered cellulose within the scope of the invention is understood to be cellulose prepared by processing alpha-cellulose obtained as a pulp from strains of fibrous plant materials, such as wood pulp.

In an advantageous embodiment of the invention, the water-insoluble composition comprises or consists of water-insoluble fiber selected from wheat fibers, oat fibers, pea fibers, powdered cellulose, or combinations thereof.

An advantage of the above embodiment may be that a relatively effective release of flavor may be facilitated. When including further substances to be released, such as e.g. nicotine, an effective release may be facilitated.

In an embodiment of the invention, the water-insoluble composition comprises or consists of water-insoluble fiber selected from wheat fibers, oat fibers, pea fibers, or combinations thereof.

In an embodiment of the invention, the water-insoluble composition comprises or consists of water-insoluble fiber selected from wheat fibers, oat fibers, or combinations thereof.

Non-limiting examples of usable water-insoluble fibers include VITACEL WF 600, VITACEL HF 600, VITACEL P95, VITACEL WF 200, VITACEL L 00, VITACEL ERBSENFASER EF 150, VITACEL BAMBOO FIBERBAF 90, VITACEL HF 600, VITACEL CELLULOSE L700G, VITACEL PF200, VITACEL POTATOFIBER KF200, VITACEL BAMBOO FIBERHAF BAF40, VITACEL HAFERFASER/OAT FIBER HF-401-30 US.

Non-limiting examples of usable powdered cellulose include VITACEL L00, VITACEL Cellulose L700G, VITACEL LC1000, VITACEL L600-20, VITACEL L600.

In an embodiment, the powdered cellulose is chemically unmodified. Thus, powdered cellulose may be chemically unmodified cellulose fibers, which do not include e.g. microcrystalline cellulose (MCC).

In an advantageous embodiment of the invention, the water-insoluble fiber has a water binding capacity of at least 200%, such as at least 300%, such as at least 400%.

An advantage of the above embodiment may be that the high water-binding capacity enables pouch compositions having a high water-content.

Furthermore, the pouches having a high water-content where found to have a desirable texture and mouthfeel may while still being able to store manufactured pouches together in abutment e.g. in cans etc. without sticking too much together to result in ruptures of the pouches when being removed.

In an embodiment of the invention, the water-insoluble fiber has a water binding capacity of 200% to 1500%, such as 300 to 1300%, such as 200 to 800%, such as 300 to 800%, such as 400 to 600%.

In an embodiment of the invention, the water-insoluble fiber has a water binding capacity of 200 to 1500%, such as 300 to 1300%, such as 300 to 900%, such as 300 to 700%, such as 400 to 700%.

In an embodiment of the invention, the water-insoluble fiber has a water binding capacity of 200 to 1500%, such as 400 to 1500%, such as 500 to 1500%, such as 500 to 1200%, such as 500 to 1000%.

In an embodiment of the invention, the water-insoluble fiber has a water binding capacity of 300 to 1500%, such as 400 to 1300%.

In an advantageous embodiment of the invention, the water-insoluble fiber has a density of 50 to 500 gram per Liter, such as 100 to 400 gram per Liter, such as 200 to 300 gram per Liter.

In an embodiment of the invention, the water-insoluble fiber has a swelling capacity of at least 5.0 mL/g, such as 5.0-20 mL/g.

An advantage of the above embodiment is that the amount of water-insoluble fiber can be reduced without compromising the mouthfeel during use. If an amount of water-insoluble fiber is substituted for a water-soluble component, the swelling of the water-insoluble fiber will during use counteract the dissolution of the water-soluble component, thereby the user will not experience any decrease in pouch content during use.

In an advantageous embodiment of the invention, the water-insoluble composition comprises or consists of water-insoluble fiber in an amount between 5 and 50% by weight of the pouch composition and a water content of 15 to 70% by weight of said pouch composition.

In an advantageous embodiment of the invention, the pouch composition comprises water in an amount of at least 5% by weight of the composition, such as at least 8% by weight of the composition, such as at least 10% by weight of the composition, such as at least 20% by weight of the composition.

In an advantageous embodiment of the invention, the pouch composition comprises water in an amount of less than 65% by weight of the pouch composition, such as less than 60% by weight of the pouch composition, such as less than 50% by weight of the pouch composition, such as less than 40% by weight of the composition.

In an advantageous embodiment of the invention, the pouch composition comprises water in an amount of 8-60% by weight of the composition, such as 8-50% by weight of the composition, such as 8-40% by weight of the composition, such as 20-40% by weight of the composition.

In an embodiment of the invention, the pouch composition comprises water in an amount of 8-65% by weight of the composition, such as 10-65% by weight of the composition, such as 15-65% by weight of the composition, such as 20-65% by weight of the composition.

In an embodiment of the invention, the pouch composition has a water content of 15 to 70% by weight of said pouch composition, such as 15 to 50% by weight of said pouch composition, such as 15 to 40% by weight of said pouch composition, such as 15 to 30% by weight of said pouch composition, such as 15 to 25% by weight of said pouch composition.

In an embodiment of the invention, the pouch composition comprises water in an amount of 8-60% by weight of the composition, such as 8-50% by weight of the composition, such as 8-40% by weight of the composition, such as 8-30% by weight of the composition.

In an advantageous embodiment of the invention, the pouch composition comprises water in an amount of 20-65% by weight of the composition, such as 20-60% by weight of the composition, such as 20-50% by weight of the composition, such as 20-40% by weight of the composition.

In an advantageous embodiment of the invention, the pouch composition comprises water and water-insoluble fiber in a weight ratio of no more than 3.0, such as no more than 2.5, such as no more than 2.0, such as no more than 1.5, such as no more than 1.0.

In an embodiment, the pouch composition comprises water and water-insoluble fiber in a weight ratio of 3.0 to 0.2, such as 2.0 to 0.2, such as 1.5 to 0.5.

Thus, the weight ratio above has in the numerator the content of water in percentage by weight of the pouch composition, and in the denominator the content water-insoluble fiber in percentage by weight of the pouch composition.

Having a water content within the scope of this invention may facilitate a fast release within an initial fast release period, such as within the first 120 seconds, such as within the first 5 minutes, since the pouch is already wetted or partly wetted with water from start of use.

On the other hand, the water content should not be too high. Having a too high water content could influence the liquid diffusion both into the pouch as well as out of the pouch. A fully wetted pouch may have a lower liquid diffusion both into and out of the pouch when used, whereas as partly wetted pouch may have higher liquid diffusion both into and out of the pouch. A pouch with a low liquid diffusion may thus have a lower release, such as a lower initial release of components such as flavor or optional active ingredient.

In an embodiment of the invention, the pouch composition has a water content of no more than 60% by weight of said pouch composition, such as no more than 50% by weight of said pouch composition, such as no more than 40% by weight of said pouch composition, such as no more than 30% by weight of said pouch composition.

In an embodiment of the invention, the pouch composition comprises a total amount of flavor composition of no more than 10% by weight of the pouch composition, such as no more than 8% by weight of the pouch composition, such as no more than 5% by weight of the pouch composition. The total amount of flavor composition is the sum of liquid flavor composition and powder flavor composition.

In an advantageous embodiment of the invention, the pouch composition comprises water-insoluble fibers selected from pea fibers, powdered cellulose, and combinations thereof, and flavor composition in an amount of no more than 10% by weight of the pouch composition.

An advantage of the above embodiment may be that a very effective release of flavor composition is facilitated by the inclusion of pea and/or powdered cellulose.

In an embodiment of the invention, the pouch composition comprises water-insoluble fibers selected from pea fibers and powdered cellulose, or a combination thereof, and a total amount of flavor composition of 0.01-10% by weight of the pouch composition.

In an embodiment of the invention, the water-soluble fiber comprises or consists of cereal fibers.

In an embodiment of the invention, the water-soluble fiber comprises or consists of fruit and/or vegetable fibers.

In an advantageous embodiment of the invention, the pouch composition further comprises nicotine.

The use of liquid flavor according to the provisions of the invention has proven very attractive from a user perspective in combination with nicotine. The use of liquid flavor according to the provisions of the invention is working very attractive in terms of e.g. liquid menthol or liquid mint flavors, in particular in embodiments where flavors are partly encapsulating or coating nicotine/nicotine-containing particles.

In an advantageous embodiment of the invention, the nicotine is selected from the group consisting of a nicotine salt, nicotine free base, nicotine bound to an ion exchanger, such as an ion exchange resin, such as nicotine polacrilex resin, a nicotine inclusion complex or nicotine in any non-covalent binding; nicotine bound to zeolites; nicotine bound to cellulose, such as microcrystalline cellulose, or starch microspheres, and mixtures thereof.

One example of a combination of different types of nicotine is the combination of free-base nicotine mixed with polacrilex resin, where some nicotine is be bound to the ion exchange resin, whereas some nicotine remains unbound.

Free base nicotine includes nicotine mixed with sugar alcohols, modified Calcium carbonate, water-soluble fibers, ion exchange resin, and any combination thereof. Nicotine bound to modified Calcium carbonate is described in international patent application WO 2010/121619, hereby incorporated by reference.

In an advantageous embodiment of the invention, the nicotine comprises non-salt nicotine.

In an advantageous embodiment of the invention, the nicotine comprises nicotine free base.

A very significant advantage of the above embodiment may be that a long shelf life of the pouched product may be obtained, with a long-life taste and texture. Providing nicotine in the free base form allows facilitates obtaining a higher pH in the pouch composition, without using too much alkaline pH adjusting agent.

Thus, in the above embodiment, the amount of alkaline pH adjusting agent may be reduced without compromising the shelf life and long-life taste and texture.

In an advantageous embodiment of the invention, the nicotine comprises nicotine mixed with ion exchange resin.

In an embodiment of the invention, the nicotine comprises nicotine mixed with ion exchange resin, such as polacrilex resin, the nicotine pouch composition further comprises nicotine bound to an ion exchange resin, i.e. a nicotine ion exchange resin complex. Thus, the nicotine may be nicotine mixed with polacrilex resin, where some nicotine is bound to the ion exchange resin, whereas some nicotine remains unbound as free-base nicotine.

In an advantageous embodiment of the invention the nicotine comprises free-base nicotine mixed with ion exchange resin in a weight ratio between the free-base nicotine and the ion exchange resin of 0.1 to 2.0, preferably from 0.5 to 2.0, and most preferred about 0.67 to 1.0.

In an embodiment of the invention the nicotine comprises free-base nicotine mixed with ion exchange resin in a weight ratio between the free-base nicotine and the ion exchange resin of 1:1 to about 1:10, preferably from 1:2 to 1:6, and most preferred about 1:4-1:5.

Here, a weight ratio refers to the ratio of the mass of the first component divided by the mass of the second component. The term mixing ratio may also be used.

Thus, in the above embodiment, the nicotine comprises free-base nicotine mixed with ion exchange resin in a weight ratio between the free-base nicotine and the ion exchange resin of 0.1 to about 1, preferably from 0.17 to 0.5, and most preferred about 0.2-0.25.

In an embodiment, the pouch composition comprises water and water-insoluble fiber in a weight ratio of 0.2 to 0.8.

In an advantageous embodiment of the invention, the nicotine comprises a nicotine salt.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

In an embodiment of the invention, the nicotine salt comprises or consists of nicotine bitartrate.

In an advantageous embodiment of the invention, the nicotine comprises nicotine bound to an ion exchange resin.

In an embodiment of the invention, the ion exchange resin is a polacrilex resin.

In an embodiment of the invention, the polacrilex resin is Amberlite® IRP64.

In an advantageous embodiment of the invention, the nicotine comprises synthetic nicotine.

In an advantageous embodiment of the invention, the nicotine comprises nicotine isolated from tobacco.

In an advantageous embodiment of the invention, the pouch composition comprises nicotine in an amount of at least 0.1% by weight, such as least 0.2% by weight of the pouch composition.

In an advantageous embodiment of the invention, the pouch composition comprises nicotine in an amount of 0.1 to 5.0% by weight of the pouch composition, such as 0.2 to 4.0% by weight of the pouch composition, such as 1.0 to 2.0% by weight of the pouch composition.

In an embodiment of the invention, the pouch composition is substantially homogenous.

Homogeneity of a pouch composition may be assessed by evaluating the distribution between individual pouches of single components of the composition.

For example, the standard deviation of the nicotine content, i.e. nicotine content uniformity (CU), relates to the homogeneity of the pouch composition. Pouches prepared from the same pouch composition and having a low standard deviation on the nicotine content will have a high pouch composition homogeneity, whereas pouches prepared from the same pouch composition and having a high standard deviation on the nicotine content will have a low pouch composition homogeneity.

In an advantageous embodiment of the invention, the content of nicotine between a series of at least 10 oral pouches comprising said pouch composition holds a relative standard deviation (RSD) below 10%, preferably below 8%, more preferably at most 6%, even more preferably at most 4%, and most preferably at most 2%.

In an embodiment of the invention, the content of the nicotine between a series of at least 10 oral pouches comprising said pouch composition holds a relative standard deviation (RSD) of 0.1-10%, preferably 0.1-8%, more preferably 0.1-6%, even more preferably 0.1-4% and most preferably 0.1-2%.

By adding the liquid flavor composition after the water has been mixed with the powdered composition, a more homogenous pouch composition is obtained.

In an advantageous embodiment of the invention, the pouch composition is free of tobacco, tobacco fibers and fibers derived from tobacco.

In some alternative embodiments, the pouch composition may comprise minor amounts of tobacco. Any, nicotine provided as part of tobacco, such as e.g. powdered tobacco, is further to the free-base nicotine.

Such tobacco may e.g. be included to provide tobacco flavor.

In an embodiment, the pouch composition may comprise tobacco, tobacco fibers, or fibers derived from tobacco in an amount of 0.1 to 5.0% by weight of the pouch composition, such as in an amount of 0.1 to 3.0% by weight of the pouch composition. Thus, while the pouch composition in some embodiments may comprise small amounts of tobacco, this is in addition to the free-base nicotine, and thus the pouch composition is not tobacco based.

In an embodiment of the invention, the pouch composition comprises less than 5.0% by weight of tobacco, such as less than 3.0% by weight of the pouch composition, such as less than 1.0% by weight of the pouch composition, such as less than 0.5% by weight of the pouch composition, such as less than 0.1% by weight of the pouch composition, such as being free of tobacco.

In an embodiment of the invention, the pouch composition does not comprise tobacco, tobacco fibers or fibers derived from tobacco. Thus, in this embodiment, the water-insoluble fibers are non-tobacco fibers, i.e. does not comprise tobacco, tobacco fibers, or fibers derived from tobacco.

In an embodiment of the invention, the pouch composition is free of microcrystalline cellulose (MCC), such as free of cellulose.

In an embodiment of the invention, the pouch composition comprises cellulose and is free of microcrystalline cellulose (MCC).

In an advantageous embodiment of the invention, the liquid flavor composition at least partially covers the surface of the powdered composition.

In an advantageous embodiment of the invention, at the liquid flavor composition is at least partially adsorbed to the surface of the powdered composition.

In an advantageous embodiment of the invention, the pouch composition has a bulk density of at most 0.8 g/cm3, such as has a bulk density of at most 0.7 g/cm3, such as at most 0.6 g/cm3, such as at most 0.5 g/cm3.

An advantage of the above embodiment may be that a low-density composition may be obtained. Unexpectedly, the combination of water and sugar alcohols did not lead to a very dense, compact and un-processable pouch composition but allowed a relatively light and low-density composition.

In an advantageous embodiment of the invention, the pouch composition has a bulk density between 0.2 g/cm3 and 0.8 g/cm3, such as between 0.3 g/cm3 and 0.7 g/cm3, such as between 0.3 g/cm3 and 0.6 g/cm3, such as between 0.4 and 0.5 g/cm3.

In an embodiment of the invention, the composition has a bulk density between 0.2 g/cm3 and 0.8 g/cm3, such as between 0.2 g/cm3 and 0.7 g/cm3, such as between 0.2 g/cm3 and 0.6 g/cm3, such as between 0.2 and 0.5 g/cm3.

In an embodiment of the invention, the composition has a bulk density between 0.2 g/cm3 and 0.8 g/cm3, such as between 0.3 g/cm3 and 0.8 g/cm3, such as between 0.4 g/cm3 and 0.8 g/cm3, such as between 0.5 and 0.8 g/cm3.

The density of the pouch composition may be affected by a number of parameters, particularly type(s) and amount(s) of sugar alcohol(s), type(s) and amount(s) of fiber(s), content of water, and processing hereunder mixing time. While varying the amount of e.g. water also affects mobility such that adding too much water results in a to compact and dense pouch formulation, selecting a fiber with higher water binding capacity may at least partly counteract a higher water content. Also, it was observed that excessive mixing could lead to a too compact and dense pouch composition.

In an advantageous embodiment of the invention, the pouch composition further comprises a pH-regulating agent, such as a basic pH-regulating agent, such as a basic buffering agent.

In an embodiment of the invention, the pouch composition further comprises a combination of at least two pH-regulating agents, such as a combination of at least two basic pH-regulating agents, such as a combination of at least two basic buffering agents, such as a basic buffer pair.

An advantage of the above embodiment may be that a more effective uptake of nicotine may be obtained, especially when using a basic (alkaline) pH regulating agent.

Another advantage of the above embodiment may be that a desirable mouthfeel may be obtained during use.

While lower amounts of pH regulating agent may be applicable in embodiments, e.g. by avoiding the use of nicotine salts, such as nicotine bitartrate, it may still be desirable to further increase the pH by adding pH regulating agent.

In an advantageous embodiment of the invention, the pouch composition comprises an alkaline buffering agent.

As used herein, the term alkaline buffering agent is used interchangeable with basic buffering agent, i.e. alkaline is used in the sense of "basic" as opposed to acidic.

In an advantageous embodiment of the invention, the pouch composition comprises the pH-regulating agent in an amount of less than 6% by weight of the pouch composition, less than 5% by weight of the pouch composition, such as less than 4% by weight of the pouch composition, such as less than 2% by weight of the pouch composition, such as less than 1% by weight of the pouch composition, such as free of pH-regulating agent.

In an embodiment of the invention, the pouch composition comprises pH-regulating agents in an amount of 0 to 6% by weight of the pouch composition, such as 0 to 5% by weight of the pouch composition, such as 0 to 4% by weight of the pouch composition, such as 0 to 3% by weight of the pouch composition, such as 0 to 2% by weight of the pouch composition such as 0 to 1% by weight of the pouch composition.

In an embodiment of the invention, the pouch composition comprises pH-regulating agents in an amount of 0.1 to 6% by weight of the pouch composition, such as in an amount of 0.1 to 5% by weight of the pouch composition, such as in an amount of 0.5 to 5% by weight of the pouch composition, such as in an amount of 0.5 to 4% by weight of the pouch composition, such as in an amount of 0.1 to 3% by weight of the pouch composition, such as in an amount of 0.1 to 2% by weight of the pouch composition, such as in an amount of 0.1 to 1% by weight of the pouch composition.

In an embodiment of the invention, the pouch composition comprises pH regulating agent, e.g. in an amount of 0.01 and 15% by weight of the pouch composition.

In an embodiment of the invention, the pouch composition comprises pH regulating agent in an amount between 0.01 and 15% by weight of the pouch composition, such as between 0.5 and 10% by weight of the pouch composition, such as between 1 and 10% by weight of the pouch composition, such as between 5 and 10% by weight of the pouch composition.

In an advantageous embodiment of the invention, the pouch composition is adapted to give a pH of at least 8.0, such as a pH of at least 8.2, such as a pH of at least 8.5, such as a pH of at least 8.7, such as a pH of at least 9.0, when 2.0 gram of pouch composition is added to 20 mL of 0.02 M potassium dihydrogen phosphate-buffer (pH adjusted to 7.4).

An advantage of the above embodiment may be that a relatively effective uptake of nicotine is facilitated due to the high pH value obtained.

A further advantage of the above embodiment may be that the need for preservative may be decreased or even eliminated and that low amounts of such preservatives may be used if not absent.

Also, the high pH value obtained may advantageously provide for a tingling sensation in the mouth which may be perceived as a desirable mouthfeel, e.g. due to resemblance with tobacco-based pouch products.

In an advantageous embodiment of the invention, the pH regulating agent is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, the pH regulating agent is a basic pH regulating agent, such as a basic buffering agent and/or such as Sodium carbonate, Sodium bicarbonate, Potassium carbonate, Potassium bicarbonate, Magnesium carbonate, or any combination thereof.

In an embodiment of the invention, the pouch composition further comprises a humectant.

The humectant may attract and retain water in the oral cavity during use. However, the humectant may additionally moderate the release of active ingredients such as nicotine, e.g. to facilitate a sustained release.

In an embodiment of the invention, the pouch composition further comprises humectant in an amount of 0.5 to 10% by weight of the pouch composition, such as 0.5 to 5% by weight of the pouch composition, such as 1-3% by weight of the pouch composition.

In an embodiment of the invention, the humectant comprises one or more from the list consisting of glycerol, propylene glycol, alginate, modified starch, hydroxypropyl cellulose, triacetin, polyethylene glycol (PEG), pectin, and xanthan gum.

In an embodiment of the invention, the pouch composition further comprises alginate.

In an embodiment of the invention, the pouch composition further comprises glycerol.

In an embodiment of the invention, the pouch composition further comprises modified starch.

In an embodiment of the invention, the pouch composition further comprises hydroxypropyl cellulose (HPC).

An advantage of the above embodiment may be that pouch composition during use provides a desirable soft texture. The alginate may e.g. be provided as a humectant, and thus attract and retain water in the oral cavity during use.

In an advantageous embodiment of the invention, the pouch composition further comprises alginate in an amount of 0.5 to 5% by weight of the pouch composition, such as 1-3% by weight of the pouch composition.

In an embodiment of the invention, the pouch composition further comprises xanthan gum.

An advantage of the above embodiment may be that pouch composition during use provides a desirable soft texture. The xanthan gum may e.g. be provided as a humectant, and thus attract and retain water in the oral cavity during use.

In an advantageous embodiment of the invention, the pouch composition comprises a glidant, such as silicon dioxide, e.g. in an amount of between 0.5 and 5% by weight, such as between 1 and 3% by weight of the composition.

In an embodiment of the invention, the glidant is selected from talc powder, colloidal silica, silicon dioxide, starch, magnesium stearate, and combinations thereof.

In an embodiment of the invention, the pouch composition further comprises a powdered flavor composition, and the powdered composition comprises at least one sugar alcohol, such as at least one sugar alcohol selected from xylitol, maltitol, mannitol, erythritol, isomalt, lactitol, and mixtures thereof.

In an embodiment of the invention, the pouch composition further comprises a powdered flavor composition, and the powdered composition comprises water-insoluble fiber.

In an embodiment of the invention, the pouch composition further comprises a powdered flavor composition, the powdered composition comprises at least one sugar alcohol, and the powdered composition comprises water-insoluble fiber.

In an embodiment of the invention, the pouch composition further comprises a powdered flavor composition, and the powdered composition comprises at least one sugar alcohol, such as at least one sugar alcohol selected from xylitol, maltitol, mannitol, erythritol, isomalt, lactitol, and mixtures thereof, the liquid flavor being at least partially adsorbed to the surface of the powdered composition.

In an embodiment of the invention, the pouch composition further comprises a powdered flavor composition, and the powdered composition comprises at least one sugar alcohol, such as at least one sugar alcohol selected from xylitol, maltitol, mannitol, erythritol, isomalt, lactitol, and mixtures thereof, the pouch composition further comprising nicotine.

In an advantageous embodiment of the invention, said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and therein the water-insoluble composition comprises or consists of water-insoluble fiber, such as a water-insoluble plant fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

In an advantageous embodiment of the invention, the membrane of the pouch comprises water insoluble fiber of different origin than the water insoluble fiber contained in the pouched product.

In an advantageous embodiment of the invention, both the water insoluble fibers of the membrane and the water-insoluble fiber of the pouch composition comprises natural fiber.

In an advantageous embodiment of the invention, both the water insoluble fibers of the membrane and the water-insoluble fiber of the pouch composition are natural fiber.

In an embodiment of the invention, the pouch composition further comprises a powdered flavor composition, and the powdered composition comprises water-insoluble fiber and at least one sugar alcohol, such as at least one sugar alcohol selected from xylitol, maltitol, mannitol, erythritol, isomalt, lactitol, and mixtures thereof, the pouch composition further comprising nicotine, the liquid flavor being at least partially adsorbed to the surface of the powdered composition.

The invention relates in a second aspect to an oral pouched product comprising a pouch, a powdered composition, and a liquid flavor composition, the liquid flavor composition covering at least part of the surface of the powdered composition.

Thus, in an embodiment the liquid flavor is at least partially adsorbed to the surface of the powdered composition.

In an embodiment of the invention, the oral pouched product of the second aspect is provided in accordance with the oral pouched product of the first aspect of the invention or any of its embodiments with the provision that the limitations of claim 1 are not adhered to.

In an embodiment of the invention, the oral pouched product of the second aspect is provided in accordance with the oral pouched product of the first aspect of the invention or any of its embodiments.

In an embodiment of the invention the pouch is a pouch membrane.

In an embodiment of the invention the pouch is a saliva-permeable membrane.

Typically, the pouch membrane comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch membrane having suitable opening dimensions in view of the pouch composition to be used, the material for the pouch membrane may be selected accordingly, e.g. comprising e.g. woven and/or non-woven fabric.

In other words, according to the various embodiments, the pouch membrane allows passage of saliva and prevents or inhibits passage of undissolved composition and the water-insoluble fibers. The pouch membrane may be of any suitable material e.g. woven or non-woven fabric (e.g. cotton, fleece etc.), heat sealable non-woven cellulose, such as long fiber paper, or other polymeric materials such as a synthetic, semi-synthetic or natural polymeric material. An example of suitable material for the pouch membrane is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

In more detail, regarding the material, the pouch membrane may be a natural, synthetic, semi-synthetic hydrophilic or hydrophobic membrane. It may be made from one or more biocompatible and physiologically acceptable polymeric material. Examples of suitable materials for the pouch membrane are cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon. Other suitable materials are mentioned herein before.

Rayon fibers (i.e. regenerated cellulose), such as viscose rayon fibers may also be used, e.g. in combination with an acrylic polymer that acts as binder in the nonwoven material and provides for heat-sealing of the pouch membrane during manufacturing thereof. Other binders, such as one or more copolymers of vinyl acetate and acrylic acid ester, may also be used.

Suitable pouch membranes for are available under the trade names TABOKA, CATCHDRY, ETTAN, GENERAL GRANIT, GOTEBORGS RAPE, GROVSNUS WHITE, METROPOL KAKTUS, MOCCA ANIS, MOCCA MINT, MOCCA WINTERGREEN, KICKS, PROBE, PRINCE, SKRUF, TREANKRARE, CAMEL SNUS ORIGINAL, CAMEL SNUS FROST and CAMEL SNUS SPICE. The pouch membrane provides a liquid-permeable container of a type that may be considered to be similar in character to the mesh-like type of material that is used for the construction of a tea bag. Desired components of the nicotine composition to be released diffuse through the pouch membrane and into the mouth of the user.

Materials of the pouch membrane may have the form of a mesh, screen, perforated paper, permeable fabric, or the like. For example, pouch material manufactured from a mesh-like form of rice paper, or perforated rice paper, may dissolve in the mouth of the user. In some exemplary embodiments, the materials of the pouch membrane may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the nicotine contents permeates through the pouch material prior to the time that the pouch undergoes loss of its physical integrity. If desired, flavoring ingredients, disintegration aids, and other desired components, may be incorporated within, or applied to, the pouch material.

Examples of various types of pouch membrane materials set forth in U.S. Pat. No. 5,167,244 to Kjerstad. Fleece materials for use as pouch membranes are described e.g. in WO 2008/152469, GB 673,587, and EP 2 692 254.

In an embodiment of the invention the membrane comprises water insoluble fiber of different origin than the water insoluble fiber contained in the pouched product.

In an embodiment of the invention both the water insoluble fiber of the membrane and the water-insoluble fiber of the pouch composition comprises natural fiber.

In an embodiment of the invention both the water insoluble fibers of the membrane and the water-insoluble fibers of the pouch composition are natural fibers.

In an advantageous embodiment of the invention, the pouch composition said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and therein the water-insoluble composition comprises or consists of water-insoluble fiber, such as a water-insoluble plant fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

The invention relates in a third aspect to a method of manufacturing an oral pouched product, the method comprising the steps of providing a powdered composition, mixing water with said powdered composition, adding liquid flavor composition to a mixture of the water and the powdered composition, adding the resulting mixture to a saliva-permeable pouch.

Thus, when the powdered composition comprises one or more sugar alcohols, the liquid flavor composition is added subsequent to the one or more sugar alcohols. Similarly, when the powdered composition comprises fibers, the liquid flavor composition is added subsequent to the one or more fibers. The powdered composition may also comprise a powdered flavor composition, and in such embodiments, the liquid flavor composition is added subsequent to the powdered flavor composition.

It is noted that the inventive application of liquid flavor is attractive when added so as to form a partial encapsulation or coating of the pouch content, in particular when the pouch content comprises sugar alcohols, which will rapidly dissolve upon the initial burst of flavor and thereby give the user, not only a very well-perceived taste impression, but also an attractive release of optional active ingredients.

In an embodiment of the invention, the method further comprises a step of sealing the pouch.

In an advantageous embodiment of the invention, nicotine is added to a mixture of the water and the powdered composition before adding the liquid flavor composition.

In an advantageous embodiment of the invention, the glidant is added after adding the liquid flavor composition.

DETAILED DESCRIPTION OF THE INVENTION

As used herein the term "pouch composition" refers to the composition for use in a pouched product, i.e. in pouches for oral use.

As used herein the term "pouch" is intended to mean a container typically formed by a web of a fibrous material enclosing a cavity. The pouch may be designed for administration of compounds such as nicotine in the oral cavity. In any case, it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the pouch composition. In order to release the flavor (i.e. flavor compound(s)) and optionally further ingredients to be released, the pouch is water-permeable so as to allow saliva from the oral cavity to penetrate the pouch and enter the cavity, where the saliva can come into contact with the flavor composition, whereby the flavor are released from the oral pouch.

Other active ingredients to be applied in the pouch composition within the scope of the invention includes but are not limited to the group consisting of phytochemicals, such as resveratrol and anthocyanin; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as re-mineralization agents, antibacterial agents, anti-caries agents, plaque acid buffering agents, tooth whiteners, stain removers or desensitizing agents; and combinations thereof.

In an embodiment of the invention, said active ingredient is selected from the group consisting of di-peptides, tri-peptides, oligo-peptides, deca-peptides, deca-peptide KSL, deca-peptide KSL-W, amino acids, proteins, or any combination thereof.

In an embodiment of the invention, said active ingredient comprise probiotic bacteria, such as lactobacilli, bifidobacteria, lactococcus, streptococcus, leuconostoccus, pediococcus or enterococcus.

As used herein the term "powder composition" refers to composition in the form of powder, i.e. as a particulate material having a relatively small particle size, for example between 1 and 1200 micrometer. Particularly, by powder composition is not meant a powdered tobacco.

As used herein the term "flavor" is understood as having its ordinary meaning within the art. Flavor is provided by the flavor compounds and may be included in a liquid or powdered flavor compositions. Thus, flavors does of course not include sweeteners (such as sugar, sugar alcohols and high intensity sweeteners), or acids providing pure acidity/sourness, nor compounds providing pure saltiness (e.g. NaCl) or pure bitterness. Flavor enhancers include substances that only provide saltiness, bitterness or sourness. If flavor enhancers are included in the pouch composition, the may be added as part of the flavor composition or separately. Flavor enhancers thus include e.g. NaCl, Citric acid, ammonium chloride etc.

As used herein the term "powdered flavor composition" refers to a flavor composition in powdered form. This includes flavors inherently in solid, powdered form and flavors immobilized to or within a powdered carrier, such as a water-soluble carrier or a water-insoluble carrier. Thus, the powdered flavor composition may comprise solid carrier and/or a flavor enhancer, but always comprise at least one flavor compound. Powdered flavor compositions include e.g. encapsulated flavors. Some powdered flavor compositions comprises several flavor components to obtain the desired flavor profile, whereas other powdered flavor composition comprise only a single flavor component.

As used herein the term "liquid flavor composition" refers to a flavor composition in liquid form. This includes flavors inherently in liquid form and flavor components that are liquid due to a liquid carrier. Thus, liquid flavor compositions do not include encapsulated flavors. The liquid flavor composition may comprise liquid carrier and/or a flavor enhancer, but always comprise at least one flavor compound. Some liquid flavor compositions comprises several flavor components to obtain the desired flavor profile, whereas other liquid flavor composition comprise only a single flavor component.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include glycerol, propylene glycol, alginate, modified starch, hydroxypropyl cellulose, triacetin, polyethylene glycol (PEG), pectin, xanthan gum, etc.

As used herein the term "water-soluble" refers to a relatively high water-solubility, for example a water-solubility of more than 5 gram of water-soluble composition or substance per 100 mL of water measured at 25 degrees Celsius and pH of 7.0. When referring to a "soluble" composition or substance, water-soluble is meant, unless otherwise stated.

As used herein the term "water-insoluble" refers to relatively low water-solubility, for example a water-solubility of less than 0.1 gram of water-soluble composition or substance per 100 mL of water measured at 25 degrees Celsius and pH of 7.0. When referring to "insoluble", water-insoluble is meant unless otherwise stated.

As used herein the term "nicotine" refers to nicotine used as a refined/isolated substance. Particularly, nicotine does not refer to tobacco materials having a content of nicotine.

As used herein the term "free-base nicotine" refers to non-protonated form of nicotine, and therefore does not include nicotine salts and nicotine provided as a complex between nicotine and an ion exchange resin. Nevertheless, the free-base nicotine may be mixed with an amount of ion exchange resin or water-soluble compositions such as sugar alcohols or water-soluble fibers. While free-base nicotine includes both free-base nicotine extracted from tobacco as well as synthetically manufactured free-base nicotine, the free-base nicotine is not provided in the form of tobacco or powdered tobacco. Typically, free-base nicotine is provided as a liquid.

As used herein the term "initial" could refer to the first minutes of use, such as the first 5 minutes of use.

Typically, the pouches comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch having suitable opening dimensions in view of the pouch composition to be used, the material for the pouch may be selected accordingly, e.g. comprising e.g. woven and/or non-woven fabric.

In other words, according to the various embodiments, the pouch forms a membrane allowing passage of saliva and prevents or inhibits passage of undissolved pouch composition. The membrane of the pouch may be of any suitable material e.g. woven or non-woven fabric (e.g. cotton, fleece etc.), heat sealable non-woven cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of flavor from the pouch.

The pouch composition is filled into pouches and is maintained in the pouch by a sealing. An ideal pouch is chemically and physically stable, it is pharmaceutically acceptable, it is insoluble in water, it can be filled with powder and sealed, and it provides a semi-permeable membrane layer which prevent the powder from leaving the bag, but permit saliva and therein dissolved or sufficiently small suspended components from the pouch composition in the pouch, such as flavor, to pass through said pouch.

The pouch may be placed in the oral cavity by the user. Saliva then enters into the pouch, and the flavor and other components, which are soluble in saliva, start to dissolve and are transported with the saliva out of the pouch into the oral cavity, where the nicotine may be absorbed.

According to an embodiment of the invention, the pouch composition comprises one or more pH-regulating agent, such as a buffering agent.

In an embodiment of the invention, said pH-regulating agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to various embodiments of the invention, one or more sugar alcohols may be included in the pouch as part of the pouch composition, e.g. as a carrier or part thereof, as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch composition comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch composition comprises sugar and/or sugarless sweetener, e.g. sugar alcohol.

In an embodiment of the invention, the pouch composition comprises sugar and/or sugarless sweeteners in the amount of 1.0 to about 80% by weight of the pouch composition, more typically constitute 5 to about 70% by weight of the pouch composition, and more commonly 10 to 30% by weight of the pouch composition or 5 to 25% by weight of the pouch composition. In some other embodiments, the sugar and/or sugarless sweeteners constitute 10 to 60% by weight of the pouch composition or 10-50% by weight of the pouch composition. Sugar and/or sugarless sweeteners may function both as a sweetener and also as a humectant. In some embodiments, inclusion of certain ingredients may limit the about amounts of sugar and/or sugarless sweeteners further. In some embodiments, the content of sugar and/or sugarless sweeteners in the pouch composition is no more than 20% by weight of the pouch composition, such as no more than 15% by weight of the pouch composition, such as no more than 10% by weight of the pouch composition, such as no more than 5% by weight of the pouch composition.

The sweeteners may often support the flavor profile of the pouch composition.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In embodiments of the invention, the pouch composition further comprises water soluble fibers. Non-limiting examples of water-soluble fibers include inulin, polydextrose, and psyllium plant fibers. Other water-soluble dietary fibers may also be used.

The pouch composition comprises at least a liquid flavor composition in the sense that it is added according to the provisions of the invention. It may be in a non-liquid state in the final pouch composition. The pouch composition may optionally further comprise a powdered flavor composition. The pouch composition may typically comprise flavor composition in amounts between 0.01 and 15% by weight of the total composition of the pouch, such as between 0.01 and 5% by weight of the total composition.

Non-exhaustive examples of flavor compounds suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, lemongrass, lime, jalapenos, chili (capsaicin), citrus, tobacco flavor, blackcurrant and plum essence. The essential oils include peppermint, spearmint, menthol, eucalyptus, clove oil, bay oil, anise, thyme, cedar leaf oil, nutmeg, and oils of the fruits mentioned above.

According to further embodiments of the invention, the pouch composition, may comprise an active pharmaceutical ingredient selected from the group consisting of antihistamines, anti-smoking agents, agents used for diabetes, decongestants, peptides, pain-relieving agents, antacids, nausea-relieving agents, statins, or any combination thereof.

In an embodiment of the invention, the active pharmaceutical ingredients are selected from the group consisting of cetirizine, levo cetirizine, nicotine, nicotine polacrilex, nicotine in combination with alkaline agents, metformin, metformin HCL, phenylephrine, GLP-1, exenatide, MC-4 receptor antagonist, PPY(3-36), deca-peptide, KSL-W (acetate), fluor, chlorhexidine, or any combination thereof.

In an embodiment of the invention, the active pharmaceutical ingredients are selected from the group consisting of:

loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylic acid, Ibuprofen, antacid, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine, or any combination thereof.

In an embodiment of the invention, the active pharmaceutical ingredient is selected from the therapeutical groups consisting of:

Antipyretic, Anti allergic, Anti-arrhythmic, Appetite suppressant, Anti-inflammatory, Broncho dilator, Cardiovascular drugs, Coronary dilator, Cerebral dilator, Peripheral vasodilator, Anti-infective, Psychotropic, Anti-manic, Stimulant, Decongestant, Gastro-intestinal sedative, Sexual dysfunction agent, Disinfectants, Anti-anginal substance, Vasodilator, Anti-hypertensive agent, Vasoconstrictor, Migraine treating agent, Anti-biotic, Tranquilizer, Anti-psychotic, Anti-tumor drug, Anticoagulant, Hypnotic, Sedative, Anti-emetic, Anti-nauseant, Anti-convulsant, Neuromuscular agent, Hyper and hypoglycaemic, Thyroid and antithyroid, Diuretic, Anti-spasmodic, Uterine relaxant, Anorectics, Spasmolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Betablocker, Teeth Whitener, Enzyme, Co-enzyme, Protein, Energy Booster, Fiber, Probiotics, Prebiotics, Antimicrobial agent, NSAID, Anti-tussives, Decongestants, Anti-histamines, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgesics, Analgetic-antipyretics, Psychopharmacological drugs, diagnostic sex hormones allergens, antifungal agents, Chronic Obstructive Pulmonary Disease (COPD) or any combination thereof.

In an embodiment of the invention, the active pharmaceutical ingredient is selected from the group consisting of: ace-inhibitors, antianginal drugs, antiarrhythrmas, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, antimanics, anti-nauseants, anti-stroke agents, anti-thyroid preparations, anti-tumor drugs, anti-viral agents, acne drugs, alkaloids, amino acid preparations, anti-tussives, antiuricemic drugs, anti-viral drugs, anabolic preparations, systemic and non-systemic antiinfective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, inmosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

In an embodiment of the invention, the active pharmaceutical ingredient is selected from the group consisting of anti-histamines, decongestants, smoking cessation aids, diabetes II agents, or any combination thereof.

In an embodiment of the invention, the active pharmaceutical ingredient is selected from the group consisting of ephedrine, pseudo ephedrine, caffeine, loratadine, sildenafil, simvastatin, sumatriptan, acetaminophen, calcium carbonate, vitamin D, ibuprofen, aspirin, alginic acid in combination with aluminum hydroxide and sodium bicarbonate, ondansetron, Tibolon, Rimonabant, Varenicline, allergens, sitagliptin or any derivatives thereof, salts thereof, isomers thereof, combinations thereof or compounds comprising one or more of these.

In various embodiments of the invention, the pouch composition comprises a release controlling composition for controlling the release of the pouch composition and/or parts thereof, such as nicotine and flavor.

The release controlling composition may, according to various embodiments, be selected from the group consisting of metallic stearates, modified calcium carbonate, hydrogenated vegetable oils, partially hydrogenated vegetable oils, polyethylene glycols, polyoxyethylene monostearates, animal fats, silicates, silicon dioxide, talc, magnesium stearates, calcium stearates, fumed silica, powdered hydrogenated cottonseed oils, hydrogenated vegetable oils, hydrogenated soya oil, emulsifiers, triglycerides, and mixtures thereof. Particularly, metallic stearates, such as magnesium stearate, may be advantageous.

The release controlling composition may be added to the pouch composition in various ways.

In an embodiment of the invention, the pouch composition is free of triglycerides.

For example, the release controlling composition may be added by full powder mixture during the last few minutes of the final mixing.

Alternatively, the release controlling composition may be added after granulation steps on a granulation premix.

Still further, the release controlling composition may be added as a fraction or even further as two or more fractions of the pouch composition. Combined with the combination of nicotine components and flavor compounds a more complex and tailored release profile of nicotine and flavor could be obtained.

The release controlling composition, such as magnesium stearate, may have a sealing effect and can be used to control the release of the nicotine and the solubility of the pouch.

EXAMPLES

Example 1A—Preparation of Pouches Designed for Administration of Nicotine

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

Example 1B—Preparation of Pouches Designed for Administration of Nicotine

The material of the pouches is manufactured using rayon fibers, such as viscose rayon staple fibers. The pouch membrane is heat sealed along its edges except for an opening in one end into an inner cavity formed by the pouch membrane.

The powder is filled into pouches and is maintained in the pouch by a sealing.

Example 2A—Pouches

Pouches PNN1-PNN5 are prepared comprising powdered compositions as outlined in table 1. The pouches are made as follows.

Powdered ingredients including powdered flavor (if any) are mixed using a planetary BEAR VARIMIXER mixer for 2 minutes. Then water is slowly added while the mixer is running, followed by addition of liquid flavor. Finally, silicon dioxide is added and then mixed for about 1 minute. The total mixing time is about 30 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The pouch material of example 1B may also be used.

The powder is filled into pouches and is maintained in the pouch by a sealing.

TABLE 1

Pouches with liquid flavor composition and varying water content.

| PNN | PNN1 | PNN2 | PNN3 | PNN4 | PNN5 |
|---|---|---|---|---|---|
| Water content [wt %] | 30 | 25 | 15 | 10 | 40 |
| Raw material | Content in weight percent | | | | |
| Xylitol | 25.9 | 30.9 | 40.9 | 45.9 | 15.9 |
| Purified water | 30 | 25 | 15 | 10 | 40 |
| Wheat fiber | 30 | 30 | 30 | 30 | 30 |
| Sodium alginate | 2.0 | 2.0 | 2.0 | 2.0 | 2.0 |

TABLE 1-continued

Pouches with liquid flavor composition and varying water content.

| PNN | PNN1 | PNN2 | PNN3 | PNN4 | PNN5 |
|---|---|---|---|---|---|
| Powdered flavor composition | 8.0 | 8.0 | 8.0 | 8.0 | 8.0 |
| Liquid flavor composition | 0.9 | 0.9 | 0.9 | 0.9 | 0.9 |
| NaCl | 0.1 | 0.1 | 0.1 | 0.1 | 0.1 |
| High intensity sweetener | 1.0 | 1.0 | 1.0 | 1.0 | 1.0 |
| Potassium sorbate | 0.1 | 0.1 | 0.1 | 0.1 | 0.1 |
| Silicon dioxide | 2.0 | 2.0 | 2.0 | 2.0 | 2.0 |
| Total | 100 | 100 | 100 | 100 | 100 |

Pouch content: 500 mg total.

The Xylitol applied is e.g. trade name XYLITAB 200.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PNN1-PNN5 show that different pouches having a water content of at least 10% by weight of the pouch composition can be made.

Example 2B—Pouches

Pouches PNN11-PNN15 are made similarly to pouches PNN1-PNN5 of example 2A. Pouches PNN11-PNN15 are prepared comprising powdered compositions as outlined in table 2.

TABLE 2

Pouches with liquid flavor composition and varying water content, but constant ratio between added water and fiber.

| PNN | PNN11 | PNN12 | PNN13 | PNN14 | PNN15 |
|---|---|---|---|---|---|
| Water content [wt %] | 30 | 25 | 15 | 10 | 35 |
| Raw material | Content in weight percent | | | | |
| Isomalt | 25.9 | 36.9 | 58.9 | 69.9 | 14.9 |
| Purified water | 30 | 25 | 15 | 10 | 35 |
| Wheat fiber | 30 | 24 | 12 | 6 | 36 |
| Sodium alginate | 2.0 | 2.0 | 2.0 | 2.0 | 2.0 |
| Powdered flavor composition | 8.0 | 8.0 | 8.0 | 8.0 | 8.0 |
| Liquid flavor composition | 1.0 | 1.0 | 1.0 | 1.0 | 1.0 |
| High intensity sweetener | 1.0 | 1.0 | 1.0 | 1.0 | 1.0 |
| Potassium sorbate | 0.1 | 0.1 | 0.1 | 0.1 | 0.1 |
| Silicon dioxide | 2.0 | 2.0 | 2.0 | 2.0 | 2.0 |
| Total | 100 | 100 | 100 | 100 | 100 |

Pouch content: 500 mg total.

The applied Isomalt is e.g. GALENIQ 720.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Sodium alginate is used as a humectant.

Other possible humectants include glycerol, propylene glycol, modified starch, hydroxypropyl cellulose, triacetin, polyethylene glycol (PEG), pectin, and xanthan gum.

Silicon dioxide is used as a glidant. Other possible glidants include e.g. magnesium stearate, starch and talc.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PNN11-PNN15 shows varying water content of at least 10% by weight of the pouch composition. The water content varies, but the ratio between the amount of added purified water and the amount of fibers remain constant.

Example 2C—Pouches

Pouches PNN21-PNN25 are made similarly to pouches PNN1-PNN5 of example 2A.

TABLE 3

Pouches with liquid flavor composition.

| | PNN 21 | PNN 22 | PNN 23 | PNN 24 | PNN 25 | PNN 26 | PNN 27 | PNN 28 |
|---|---|---|---|---|---|---|---|---|
| Water content [wt %] | 30 | 30 | 30 | 30 | 30 | 30 | 30 | 30 |
| Raw material | | | Content in weight percent | | | | | |
| Isomalt | — | 25.9 | — | — | — | 15.9 | — | — |
| Erythritol | — | — | 25.9 | — | — | — | 15.9 | 15.9 |
| Maltitol | — | — | — | 25.9 | — | — | — | — |
| Xylitol | 25.9 | — | — | — | — | 10 | 13.5 | 17 |
| Purified water | 30 | 30 | 30 | 30 | 43 | 30 | 30 | 30 |
| MCC (Avicel 102) | 30 | — | — | — | — | — | — | — |
| Wheat fiber | — | 30 | 30 | 30 | 43 | 30 | 30 | 30 |
| Sodium alginate | 2.0 | 2.0 | 2.0 | 2.0 | 2.0 | 2.0 | 2.0 | 2.0 |
| Powdered flavor composition | 8.0 | 8.0 | 8.0 | 8.0 | 7.9 | 8.0 | 4.0 | — |
| Liquid flavor composition | 1.0 | 1.0 | 1.0 | 1.0 | 1.0 | 1.0 | 1.5 | 2.0 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

Pouch content: 500 mg total.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate is used as a humectant.

Other possible humectants include glycerol, propylene glycol, modified starch, hydroxypropyl cellulose, triacetin, polyethylene glycol (PEG), pectin, and xanthan gum.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PNN21-PNN24 shows the use different sugar alcohols.

Pouch PNN21 further shows use of microcrystalline cellulose (MCC) instead of wheat fibers.

Pouches PNN25 is without sugar alcohol.

Pouches PNN26-PNN28 shows combination of two sugar alcohols and varying amounts of liquid and as well as powdered flavor composition, if any.

Example 2D—Pouches

Pouches PNN30, PNN31 and Comp. P1 are made similarly to pouches PNN1-PNN5 of example 2A. Pouch Comp. P2 is made similarly to pouches PPC1-5 described in example 4A.

TABLE 4

The nicotine premix II comprises 34.1 wt % water, thereby contributing to the total water content.

| PNN | PNN30 | PNN31 | Comp. P1 | Comp. P2 |
|---|---|---|---|---|
| Amount of nicotine | — | — | — | 9.6 mg |
| Water content [wt %] | 30 | 30 | 30 | 30 |
| Raw material | | Content in weight percent | | |
| Nicotine premix II (see example 3B) | — | — | — | 14.6 |
| Xylitol | 23.4 | 22.9 | 21.9 | 12.3 |
| Purified water | 30 | 30 | 30 | 25 |
| Wheat fiber | 30 | 30 | 30 | 30 |
| Sodium alginate | 2.0 | — | 2.0 | 2.0 |
| Sodium carbonate | 5.0 | 5.0 | 5.0 | 5.0 |
| Powdered flavor composition | 5.0 | 8.0 | 8.0 | 8.0 |
| Liquid flavor composition | 1.5 | 1.0 | — | — |
| High intensity sweetener | 1.0 | 1.0 | 1.0 | 1.0 |

TABLE 4-continued

The nicotine premix II comprises 34.1 wt % water, thereby contributing to the total water content.

| PNN | PNN30 | PNN31 | Comp. P1 | Comp. P2 |
|---|---|---|---|---|
| Potassium sorbate | 0.1 | 0.1 | 0.1 | 0.1 |
| Silicon dioxide | 2.0 | 2.0 | 2.0 | 2.0 |
| Total | 100 | 100 | 100 | 100 |

Pouch content: 500 mg total.

Wheat fiber, trade name VITACEL 600 WE PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

Sodium alginate is used as a humectant.

Other possible humectants include glycerol, propylene glycol, modified starch, hydroxypropyl cellulose, triacetin, polyethylene glycol (PEG), pectin, and xanthan gum.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PNN31 shows a pouch without alginate.

Pouch Comp. P1-P2 show comparable pouches with only powdered flavor, with and without nicotine.

Example 3A—Nicotine Premix I—Resin

A Stephan mixer (vacuum premixing) was charged with water, and nicotine was weighed and added, the mixer was closed and stirred for 5 minutes. Then ion exchange resin Amberlite® RP64 was weighed and added to the mixer. The mixer was closed and stirred for 10-60 minutes.

Thereby, a mixture of nicotine and cation exchange resin was produced from the constituents stated in the below table 5.

TABLE 5

Ingredients used to manufacture nicotine premix I.

| Constituent | Amount (kg) | Amount (%) |
|---|---|---|
| Nicotine | 1.0 | 5.7 |
| Water | 12.5 | 71.4 |
| Resin | 4.0 | 22.9 |
| Total | 17.5 | 100.0 |

Nicotine:resin ratio: 1:4 (0.25)
% water in obtained nicotine-resin composition: 71.4

Example 3B—Nicotine Premix II—Resin

A 60 liter planetary BEAR VARIMIXER mixer was charged with water, and nicotine was weighed and added. The mixer was stirred at low speed for 1 minute at ambient temperature. Then ion exchange resin Amberlite® RP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 6.

TABLE 6

Ingredients used to manufacture nicotine premix II.

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

Nicotine:resin ratio: 1:4 (0.25)
% water in obtained nicotine-resin composition: 34.1
The total process time was 20 minutes.

Example 3C— Nicotine Premix III—Resin

A 60 liter planetary BEAR VARIMIXER mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 7.

TABLE 7

Ingredients used to manufacture nicotine premix III.

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

Nicotine:resin ratio: 1:4 (0.25)
% water in obtained nicotine-resin composition: 7.5
The total process time was 20 minutes.

Example 3D—Nicotine Premix IV—Resin

A 60 liter planetary BEAR VARIMIXER mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 8A.

TABLE 8A

Ingredients used to manufacture nicotine premix IV.

| Constituent | Amount (kg) | Amount (%) |
|---|---|---|
| Nicotine | 1.08 | 10.0 |
| Water | 5.40 | 50.0 |
| Resin | 4.32 | 40.0 |
| Total | 10.8 | 100.0 |

Nicotine:resin ratio: 1:4 (0.25)
% water in obtained nicotine-resin composition: 50.0
The total process time was 20 minutes

Example 2E—Nicotine Premix V—Resin

A60 liter planetary BEAR VARIMIXER mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 8B.

TABLE 8B

Ingredients used to manufacture nicotine premix V.

| Constituent | Amount (kg) | Amount (%) |
|---|---|---|
| Nicotine | 1.78 | 20.0 |
| Water | 2.80 | 31.5 |
| Resin | 4.32 | 48.5 |
| Total | 8.90 | 100.0 |

Nicotine:resin ratio: 1:2.43 (0.41)
% water in obtained nicotine-resin composition: 31.5
The total process time was 20 minutes.

Example 2F—Nicotine Premix VI—Resin

A60 liter planetary BEAR VARIMIXER mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 8C.

TABLE 8C

Ingredients used to manufacture nicotine premix V.

| Constituent | Amount (kg) | Amount (%) |
|---|---|---|
| Nicotine | 3.05 | 30.0 |
| Water | 2.80 | 27.5 |
| Resin | 4.32 | 42.5 |
| Total | 10.17 | 100.0 |

Nicotine:resin ratio: 1:1.4 (0.71)
% water in obtained nicotine-resin composition: 27.5
The total process time was 20 minutes.

Example 2G—Nicotine Premix VII—Resin

A60 liter planetary BEAR VARIMIXER mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 8D.

TABLE 8D

Ingredients used to manufacture nicotine premix V.

| Constituent | Amount (kg) | Amount (%) |
|---|---|---|
| Nicotine | 5.15 | 42.0 |
| Water | 2.80 | 22.8 |
| Resin | 4.32 | 35.2 |
| Total | 12.27 | 100.0 |

Nicotine:resin ratio: 1.19:1 (1.19)
% water in obtained nicotine-resin composition: 22.8
The total process time was 20 minutes.

Example 2H—Nicotine Premix VIII—Resin

A60 liter planetary BEAR VARIMIXER mixer was charged with water, and nicotine was weighed and added. The mixer was stirred at low speed for 1 minute at ambient temperature. Then ion exchange resin Amberlite® IRP64 and fiber were weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 9.

TABLE 9

Ingredients used to manufacture nicotine premix V.

| Constituent | Amount (kg) | Amount (%) |
|---|---|---|
| Nicotine | 5.15 | 39.8 |
| Water | 2.80 | 21.6 |

TABLE 9-continued

Ingredients used to manufacture nicotine premix V.

| Constituent | Amount (kg) | Amount (%) |
|---|---|---|
| Resin | 4.32 | 33.4 |
| Pea fiber | 0.67 | 5.2 |
| Total | 12.94 | 100.0 |

Nicotine:resin ratio: 1.19:1 (1.19)
% water in obtained nicotine-resin composition: 21.6
The total process time was 20 minutes.

Example 4A—Pouches

The pouches PPC6 and PPC7 are made as follows.

Fibers and water are mixed using a planetary BEAR VARIMIXER mixer for 5 minutes. Then, the following ingredients were added subsequently under continuous mixing: first Nicotine bitartrate xH2O (NBT, nicotine content of 32.5%) or nicotine polacrilex resin (NPR, nicotine content of 15.9%) as applicable (mixed for 2 minutes), then the remaining ingredients except liquid flavor composition and glidant if any (mixed for 2 minutes), then liquid flavor composition (mixed for 1 minute), then glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention. The pouch material of example 1B may also be used.

The powder is filled into pouches and is maintained in the pouch by a sealing.

Pouches PPC1-PPC5 containing nicotine premix are prepared comprising powdered compositions as outlined in table 10. The pouches are made as follows.

Fibers and water are mixed using a planetary BEAR VARIMIXER mixer for 5 minutes. Then, the following ingredients were added subsequently under continuous mixing: Nicotine premix (mixed for 2 minutes), then the remaining ingredients except liquid flavor composition and glidant if any (mixed for 2 minutes), then liquid flavor composition (mixed for 1 minute), then glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing. The pouch material of example 1B may also be used.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

TABLE 10

The nicotine premix II (example 3B) comprises 34.1 wt % water, thereby contributing to the total water content.

| | PPC1 | PPC2 | PPC3 | PPC4 | PPC5 | PPC6 | PPC7 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 25 | 15 | 10 | 40 | 30 | 30 |
| Raw material | Content in weight percent | | | | | | |
| NPR | — | — | — | — | — | — | 12.1 |
| NBT | — | — | — | — | — | 5.9 | — |
| Nicotine premix II | 14.6 | 14.6 | 14.6 | 14.6 | 14.6 | — | — |
| Xylitol | 11.3 | 16.3 | 26.3 | 31.3 | 1.3 | 15.0 | 8.8 |
| Purified water | 25 | 20 | 10 | 5 | 35 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Powdered flavor composition | 8.0 | 8.0 | 8.0 | 8.0 | 8.0 | 8.0 | 8.0 |
| Liquid flavor composition | 0.9 | 0.9 | 0.9 | 0.9 | 0.9 | 0.9 | 0.9 |
| NaCl | 0.1 | 0.1 | 0.1 | 0.1 | 0.1 | 0.1 | 0.1 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Pouch content: 500 mg total, i.e. nicotine conc 19.2 mg/g

The Xylitol applied is e.g. trade name XYLITAB 200.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate is used as a humectant.

Other possible humectants include glycerol, propylene glycol, modified starch, hydroxypropyl cellulose, triacetin, polyethylene glycol (PEG), pectin, and xanthan gum.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC1-5 show that different pouches having a water content of at least 10% by weight of the pouch composition can be made using free-base nicotine. Pouches PPC6, PPC7 have a similar water content as PPC1, but uses nicotine salt and nicotine in complex with an ion exchange resin.

Example 4B—Pouches

Pouches PPC11-PPC15 containing nicotine premix are prepared comprising powdered compositions as outlined in table 11. The pouches are made as follows.

Fibers and powder ingredients (except glidants) are mixed using a planetary BEAR VARIMIXER mixer for 2 minutes. Then, Nicotine premix is added and mixed for 2 minutes. Water is then added and mixed for 5 minutes followed by liquid flavor composition (mixed for 1 minute) and glidant (if any—mixed for 1 minute). The total mixing time is 9-11 minutes.

TABLE 11

The nicotine premix II comprises 34.1 wt % water, thereby contributing to the total water content.

| | PPC | | | | |
|---|---|---|---|---|---|
| | PPC11 | PPC12 | PPC13 | PPC14 | PPC15 |
| Amount of nicotine | 9.6 mg | 9.6 mg | 9.6 mg | 9.6 mg | 9.6 mg |
| Water content [wt %] | 30 | 25 | 15 | 10 | 35 |
| Raw material | Content in weight percent | | | | |
| Nicotine premix II | 14.6 | 14.6 | 14.6 | 14.6 | 14.6 |
| Isomalt | 11.3 | 22.3 | 44.3 | 55.3 | 0.3 |
| Purified water | 25 | 20 | 10 | 5 | 30 |
| Wheat fiber | 30 | 24 | 12 | 6 | 36 |
| Sodium alginate | 2.0 | 2.0 | 2.0 | 2.0 | 2.0 |
| Sodium carbonate | 5.0 | 5.0 | 5.0 | 5.0 | 5.0 |
| Powdered flavor composition | 8.0 | 8.0 | 8.0 | 8.0 | 8.0 |
| Liquid flavor composition | 1.0 | 1.0 | 1.0 | 1.0 | 1.0 |
| High intensity sweetener | 1.0 | 1.0 | 1.0 | 1.0 | 1.0 |

TABLE 11-continued

The nicotine premix II comprises 34.1 wt % water, thereby contributing to the total water content.

| | PPC | | | | |
|---|---|---|---|---|---|
| | PPC11 | PPC12 | PPC13 | PPC14 | PPC15 |
| Potassium sorbate | 0.1 | 0.1 | 0.1 | 0.1 | 0.1 |
| Silicon dioxide | 2.0 | 2.0 | 2.0 | 2.0 | 2.0 |
| Total | 100 | 100 | 100 | 100 | 100 |

Pouch content: 500 mg total.

The applied Isomalt e.g. GALENIQ 720.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate is used as a humectant.

Other possible humectants include glycerol, propylene glycol, modified starch, hydroxypropyl cellulose, triacetin, polyethylene glycol (PEG), pectin, and xanthan gum.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC11-PPC13, PPC15 shows varying water content of at least 10% by weight of the pouch composition. The water content varies, but the ratio between the amount of added purified water and the amount of fibers remain constant.

Example 4C—Pouches

Pouches PPC21-PPC25 are made similarly to pouches PPC11-PPC15 of example 4B.

TABLE 12

| | PPC | | | | | | | |
|---|---|---|---|---|---|---|---|---|
| | PPC 21 | PPC 22 | PPC 23 | PPC 24 | PPC 25 | PPC 26 | PPC 27 | PPC 28 |
| Amount of nicotine | 9.6 mg | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 | 30 |

TABLE 12-continued

| | PPC | | | | | | | |
|---|---|---|---|---|---|---|---|---|
| | PPC 21 | PPC 22 | PPC 23 | PPC 24 | PPC 25 | PPC 26 | PPC 27 | PPC 28 |
| Raw material | Content in weight percent | | | | | | | |
| Nicotine premix II | 14.6 | 7.3 | 14.6 | 14.6 | 14.6 | 14.6 | 14.6 | 14.6 |
| Liquid nicotine* | — | 1.0 | — | — | — | — | — | — |
| Xylitol | 11.3 | 15.1 | 16.3 | 13.3 | 11.4 | 9.4 | 18.3 | 19.8 |
| Purified water | 25 | 27.5 | 25 | 25 | 25 | 25 | 25 | 25 |
| MCC (Avicel 102) | 30 | — | — | — | — | — | — | — |
| Wheat fiber | — | 30 | 30 | 30 | 30 | 30 | 30 | 30 |
| Sodium alginate | 2.0 | 2.0 | 2.0 | 2.0 | 2.0 | 2.0 | 2.0 | 2.0 |
| Sodium carbonate | 5.0 | 5.0 | — | 3.0 | 5.0 | 7.0 | 5.0 | 5.0 |
| Powdered flavor composition | 8.0 | 8.0 | 8.0 | 8.0 | 8.0 | 8.0 | — | 5.0 |
| Liquid flavor composition | 1.0 | 1.0 | 1.0 | 1.0 | 1.0 | 1.0 | 2.0 | 1.5 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | — | — | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

*Liquid nicotine is added as a nicotine-sugar alcohol premix in powder form.
The nicotine premix II comprises 34.1 wt % water, thereby contributing to the total water content.

Pouch content: 500 mg total.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate is used as a humectant.

Other possible humectants include glycerol, propylene glycol, modified starch, hydroxypropyl cellulose, triacetin, polyethylene glycol (PEG), pectin, and xanthan gum.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC21 shows the use of e.g. microcrystalline cellulose (MCC) instead of wheat fibers.

Pouch PPC22 shows the use of a combination of nicotine-ion exchange resin premix and nicotine-sugar alcohol premix.

Pouches PPC23-PPC26 shows the use of different amounts of buffering agent (here sodium carbonate). For high amounts of basic buffering agents, achieving a more alkaline environment, there is less need for a preservative (here potassium sorbate), therefore it is omitted in PPC25-PPC26, having the highest amounts of alkaline buffering agents.

Pouch PPC27 shows the use of a only liquid flavor composition.

Pouch PPC28 shows the use of varying amount of liquid and powdered flavor.

Example 4D—Pouches

Pouches PPC31-PPC32 are made similarly to pouches PPC1-PPC5 of example 4A, but using nicotine premix I and III, respectively.

Pouches PPC33-PPC37 are made as described below.

The nicotine and sugar alcohol (xylitol, sorbitol, maltitol or other) are weighed. The nicotine is slowly added to the sugar alcohol powder under stirring (KITCHENAID mixer operated at about 30 RPM in about 30 minutes). The resulting granulate is sieved and placed on a tray. The resulting powder is dried at ambient temperature overnight and is thereafter sieved to obtain a nicotine-sugar alcohol premix. It is also possible to add an amount of water to the nicotine before mixing with the sugar alcohol. Any such water will then be evaporated during the drying.

Fibers and water are mixed using a planetary BEAR VARIMIXER mixer for 5 minutes. Then, the following ingredients were added subsequently under continuous mixing: Powder ingredients other than nicotine premix (mixed for 2 minutes), nicotine-sugar alcohol premix (mixed for 2 minutes), then liquid flavor composition (mixed for 1 minute) and finally glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing. The pouch material of example 1B may also be used.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

TABLE 13

| | PPC | | | | | | |
|---|---|---|---|---|---|---|---|
| | PPC 31 | PPC 32 | PPC 33 | PPC 34 | PPC 35 | PPC 36 | PPC 37 |
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | | | Content in weight percent | | | | |
| Nicotine premix I | 33.7 | — | — | — | — | — | — |
| Nicotine premix III | — | 10.4 | — | — | — | — | — |
| Liquid nicotine* | — | — | 1.9 | 1.9 | 1.9 | 1.9 | 1.9 |
| Isomalt | 11.2 | 11.3 | 19.0 | — | — | — | — |
| Sorbitol | — | — | — | 19.0 | — | — | — |
| Maltitol | — | — | — | — | 19.0 | — | — |
| Inulin | — | — | — | — | — | 19.0 | — |
| Polydextrose | — | — | — | — | — | — | 19.0 |
| Purified water | 6 | 29.2 | 30 | 30 | 30 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Powdered flavor composition | 8.0 | 8.0 | 8.0 | 8.0 | 8.0 | 8.0 | 8.0 |
| Liquid flavor composition | 1.0 | 1.0 | 1.0 | 1.0 | 1.0 | 1.0 | 1.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

*Liquid nicotine is added as a nicotine-sugar alcohol premix or as a nicotine-water-soluble fiber premix in powder form.
The nicotine premix I comprises 71.4 wt % water, thereby contributing to the total water content.
The nicotine premix II comprises 34.1 wt % water, thereby contributing to the total water content.
The nicotine premix III comprises 7.5 wt % water, thereby contributing to the total water content.

Pouch content: 500 mg total.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate is used as a humectant.

Other possible humectants include glycerol, propylene glycol, modified starch, hydroxypropyl cellulose, triacetin, polyethylene glycol (PEG), pectin, and xanthan gum.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC31-PPC32 show use of other nicotine premixes.

Pouches PPC33-PPC35 show use of nicotine pre-mixed with different sugar alcohol.

Pouches PPC36-PPC37 show use of nicotine pre-mixed with different water-soluble fibers.

Example 4E—Pouches

Pouches PPC41-PPC46 are made similarly to pouches PPC1-PPC5 of example 4A.

TABLE 14

The nicotine premix II comprises 34.1 wt % water, thereby contributing to the total water content.

| PPC | PPC41 | PPC42 | PPC43 | PPC44 | PPC45 | PPC46 |
|---|---|---|---|---|---|---|
| Amount of nicotine | 4.8 mg | 7.2 mg | 9.6 mg | 12 mg | 9.6 mg | 9.6 mg |
| Water content [wt %] | 27.5 | 28.3 | 30 | 31.2 | 30 | 30 |
| Raw material | | | Content in weight percent | | | |
| Nicotine premix II | 7.3 | 9.7 | 14.6 | 18.3 | 14.6 | 14.6 |
| Xylitol | 18.6 | 16.2 | 11.3 | 7.6 | 13.3 | 5 |
| Erythritol | — | — | — | — | — | 6.3 |
| Purified water | 25 | 25 | 25 | 25 | 25 | 25 |
| Wheat fiber | 30 | 30 | 30 | 30 | 30 | 30 |
| Sodium alginate | 2.0 | 2.0 | 2.0 | 2.0 | — | 2.0 |

TABLE 14-continued

The nicotine premix II comprises 34.1 wt % water,
thereby contributing to the total water content.

| PPC | PPC41 | PPC42 | PPC43 | PPC44 | PPC45 | PPC46 |
|---|---|---|---|---|---|---|
| Sodium carbonate | 5.0 | 5.0 | 5.0 | 5.0 | 5.0 | 5.0 |
| Powdered flavor composition | 8.0 | 8.0 | 8.0 | 8.0 | 8.0 | 8.0 |
| Liquid flavor composition | 1.0 | 1.0 | 1.0 | 1.0 | 1.0 | 0.9 |
| NaCl | — | — | — | — | — | 0.1 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

Pouch content: 500 mg total.

Wheat fiber, trade name VITACEL 600 WE PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers, bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate is used as a humectant.

Other possible humectants include glycerol, propylene glycol, modified starch, hydroxypropyl cellulose, triacetin, polyethylene glycol (PEG), pectin, and xanthan gum.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC41-PPC44 show use of different doses of nicotine, from 4.8 mg to 12 mg.

Pouch PPC45 shows pouch without alginate, otherwise comparable to pouch PPC43.

Pouch PPC46 shows pouch comprising two sugar alcohols.

Example 4F—Pouches

Pouches PPC51-PPC53 are made as follows.

Fibers and powder ingredients (except nicotine containing powders and glidants) are mixed for 1 minute using a planetary BEAR VARIMIXER mixer. Then, NPR and NBT is added and mixed for 2 minutes (if applicable). Nicotine premix is then added and mixed for 2 minutes. Subsequently, water is added and mixed for 5 minutes followed by liquid flavor composition (mixed for 1 minute) and glidant (if any—mixed for 1 minute). The total mixing time is 9-11 minutes.

TABLE 15

The nicotine premix 11 comprises 34.1 wt % water,
thereby contributing to the total water content.

| PPC | PPC51 | PPC52 | PPC53 |
|---|---|---|---|
| Amount of nicotine | 9.6 mg | 9.6 mg | 9.6 mg |
| Water content [wt %] | 30 | 30 | 30 |
| Raw material | Content in weight percent | | |
| NPR | — | 6.0 | 3.0 |
| NBT | 2.9 | — | 1.5 |
| Nicotine premix II | 7.3 | 7.3 | 7.3 |
| Isomalt | 15.2 | 12.1 | 13.6 |
| Purified water | 27.5 | 27.5 | 27.5 |
| Wheat fiber | 30 | 30 | 30 |
| Sodium carbonate | 5.0 | 5.0 | 5.0 |
| Powdered flavor composition | 8.0 | 8.0 | 8.0 |
| Liquid flavor composition | 1.0 | 1.0 | 1.0 |
| High intensity sweetener | 1.0 | 1.0 | 1.0 |
| Potassium sorbate | 0.1 | 0.1 | 0.1 |
| Silicon dioxide | 2.0 | 2.0 | 2.0 |
| Total | 100 | 100 | 100 |

Pouch content: 500 mg total.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bran fibers bamboo fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC51 shows pouch using nicotine-ion exchange resin premix in combination with nicotine bitartrate (NBT).

Pouch PPC52 shows pouch using nicotine-ion exchange resin premix in combination with nicotine polacrilex resin (NPR).

Pouch PPC53 shows pouch using nicotine-ion exchange resin premix in combination with nicotine bitartrate (NBT) and nicotine polacrilex resin (NPR).

Example 4G—Pouches

Pouches PNN1-PNN5, PNN11-PNN15, PNN21-PNN27, PNN31, PPC11-PPC15, PPC21-PPC26, PPC31-PPC37, PPC41-PPC46, and PPC51-PPC53 were also made in versions with a mint liquid flavor composition combined with a mint powdered flavor composition, with a lemon liquid flavor composition combined with a lemon powdered flavor composition further comprising citric acid as a flavor enhancer, and with a mint liquid flavor composition combined with a menthol powdered flavor composition further comprising sodium chloride and ammonium chloride as flavor enhancers.

Example 4H—Pouches

Pouches PPC61-PPC67 containing nicotine premix are prepared comprising powdered compositions as outlined in table 16. The pouches are made as follows.

Fibers and powder ingredients (except glidants) are mixed using a LODIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

TABLE 16

The nicotine premix VI comprises 27.5 wt % water, thereby contributing to the total water content.

| PPC | PPC 61 | PPC 62 | PPC 63 | PPC 64 | PPC 65 | PPC 66 | PPC 67 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | | | Content in weight percent | | | | |
| Nicotine premix VI | 6.4 | 6.4 | 6.4 | 6.4 | 6.4 | 6.4 | 6.4 |
| Xylitol | 5 | 18.3 | 18.3 | 18.3 | 5 | 5 | 5 |
| Erythritol | 13.5 | — | — | — | 13.5 | 13.5 | 13.5 |
| Purified water | 28 | 28 | 28 | 28 | 28 | 28 | 28 |
| Wheat fiber | 30 | 30 | 20 | 40 | 30 | 30 | 30 |
| Sodium alginate | 2.0 | 2.0 | 2.0 | 2.0 | 2.0 | — | — |
| Glycerol | — | — | — | — | — | 2.0 | — |
| Hydroxypropyl cellulose | — | — | — | — | — | — | 2.0 |
| Sodium carbonate | 5.0 | 3.0 | 3.0 | 3.0 | 3.0 | 3.0 | 3.0 |
| Sodium bicarbonate | — | 2.0 | 2.0 | 2.0 | 2.0 | 2.0 | 2.0 |
| Powdered flavor | 6.0 | 6.0 | 6.0 | 6.0 | 6.0 | 6.0 | 6.0 |
| Liquid flavor | 1.0 | 1.0 | 1.0 | 1.0 | 1.0 | 1.0 | 1.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Pouch content: 500 mg total.

Wheat fiber, trade name VITACEL 600 WF PLUS. Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, powdered cellulose, bamboo fibers, bran fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC61-PPC62 show use of different sweetener and buffer combinations.

Pouches PPC63-PPC64 show pouches with varying fiber content.

Pouches PPC65-PPC67 show use of different humectants.

Example 4I—Pouches

Pouches PPC71-PPC76 containing nicotine premix are prepared comprising powdered compositions as outlined in table 17. The pouches are made as follows.

Fibers and powder ingredients (except glidants) are mixed using a LODIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1A, made from long fiber paper, is used. The powder is filled into pouches and is maintained in the pouch by a sealing. The pouch material of example 1B may also be used.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

TABLE 17

The nicotine premixes comprise water in varying amount, thereby contributing to the total water content.

| PPC | PPC 71 | PPC 72 | PPC 73 | PPC 74 | PPC 75 | PPC 76 | PPC 77 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | | | Content in weight percent | | | | |
| Nicotine premix IV | 19.2 | — | — | — | — | — | — |
| Nicotine premix V | — | 9.6 | — | — | — | — | — |
| Nicotine premix VI | — | — | — | — | 6.4 | 6.4 | 6.4 |
| Nicotine premix VII | — | — | 4.6 | — | — | — | — |
| Nicotine premix VIII | — | — | — | 4.8 | — | — | — |
| Purified water | 21 | 27 | 29 | 29 | 28 | 28 | 28 |
| Wheat fiber | 30 | 30 | 30 | 29.75 | — | — | — |
| Oat fiber | — | — | — | — | 30 | — | — |
| Pea fiber | — | — | — | 0.25 | — | 30 | — |
| Powdered cellulose | — | — | — | — | — | — | 30 |
| Xylitol DC | 5.0 | 5.0 | 5.0 | 5.0 | 5.0 | 5.0 | 5.0 |
| Erythritol | 7.7 | 11.3 | 14.3 | 14.1 | 13.5 | 13.5 | 13.5 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Powdered flavor | 6.0 | 6.0 | 6.0 | 6.0 | 6.0 | 6.0 | 6.0 |
| Liquid flavor | 1.0 | 1.0 | 1.0 | 1.0 | 1.0 | 1.0 | 1.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Nicotine premix VIII comprises peafiber.

Pouch content: 500 mg total, i.e. nicotine conc 19.2 mg/g.

Wheat fiber, trade name VITACEL 600 WF PLUS.

Powdered cellulose, trade name "VITACEL LOO" or "VITACEL L700G".

Oat fiber, trade name "VITACEL HF 600".

Pea fiber, trade name "VITACEL EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bamboo fibers, powdered cellulose, bran fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Acesulfame potassium and/or sucralose may as an example be used as high intensity sweeteners. Other usable high intensity sweeteners described herein may be used in combination with or instead of acesulfame potassium and/or sucralose.

Pouches PPC71-PPC74 show use of different nicotine premixes.

Pouches PPC75-PPC77 show use of different fibers.

Example 4J—Pouches

Pouches PPC81-PPC94 containing nicotine premix are prepared comprising powdered compositions as outlined in table 18A and 18B. The pouches are made as follows.

Fibers and powder ingredients (except glidants) are mixed using a LODIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example A, made from long fiber paper, is used. The powder is filled into pouches and is maintained in the pouch by a sealing. The pouch material of example 1B may also be used.

TABLE 18A

| PPC | PPC 81 | PPC 82 | PPC 83 | PPC 84 | PPC 85 | PPC 86 | PPC 87 | PPC 88 |
|---|---|---|---|---|---|---|---|---|
| Amount of nicotine | 9.6 mg | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 | 30 |
| Raw material | Content in weight percent | | | | | | | |
| Nicotine premix II | 14.6 | 14.6 | 14.6 | 14.6 | — | — | — | — |
| Nicotine premix VI | — | — | — | — | 6.4 | 6.4 | 6.4 | 6.4 |
| Purified water | 25 | 25 | 25 | 25 | 28 | 28 | 28 | 28 |
| Wheat fiber | 30 | — | — | — | — | — | — | 15 |
| Oat fiber | — | 30 | — | — | 15 | — | — | — |
| Pea fiber | — | — | 30 | — | — | 15 | — | — |
| Powdered cellulose | — | — | — | 30 | — | — | 15 | — |
| Xylitol DC | 5.0 | 5.0 | 5.0 | 5.0 | 5.0 | 5.0 | 5.0 | 5.0 |
| Erythritol | 8.3 | 8.3 | 8.3 | 8.3 | 28.5 | 28.5 | 28.5 | 28.5 |
| Sodium alginate | 2.0 | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 | 5.0 |
| Powdered flavor | 6.0 | 6.0 | 6.0 | 6.0 | 6.0 | 6.0 | 6.0 | 6.0 |
| Liquid flavor | 1.0 | 1.0 | 1.0 | 1.0 | 1.0 | 1.0 | 1.0 | 1.0 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

TABLE 18B

| PPC | PPC 89 | PPC 90 | PPC 91 | PPC 92 | PPC 93 | PPC 94 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |
| Raw material | Content in weight percent | | | | | |
| Nicotine premix II | 14.6 | 14.6 | 14.6 | 14.6 | — | — |
| Nicotine premix VI | — | — | — | — | 6.4 | 6.4 |
| Purified water | 25 | 25 | 25 | 25 | 28 | 28 |
| Wheat fiber | 15 | — | — | — | 15 | 15 |
| Oat fiber | — | 15 | — | — | — | — |
| Pea fiber | — | — | 15 | — | — | — |
| Powdered cellulose | — | — | — | 15 | — | — |
| Xylitol DC | 5.0 | 5.0 | 5.0 | 5.0 | 5.0 | 5.0 |
| Erythritol | 23.3 | 23.3 | 23.3 | 23.3 | 28.5 | 20.5 |
| Sodium alginate | 2.0 | 2.0 | 2.0 | 2.0 | — | — |
| NaCl | — | — | — | — | — | 10 |
| Sodium carbonate | 5.0 | 5.0 | 5.0 | 5.0 | 3.5 | 5.0 |
| Sodium bicarbonate | — | — | — | — | 3.5 | — |
| Powdered flavor | 6.0 | 6.0 | 6.0 | 6.0 | 6.0 | 6.0 |
| Liquid flavor | 1.0 | 1.0 | 1.0 | 1.0 | 1.0 | 1.0 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premixes comprise water in varying amount, thereby contributing to the total water content.

Pouch content: 500 mg total, i.e. nicotine conc 19.2 mg/g.

Wheat fiber, trade name "VITACEL 600 WF PLUS" or "VITACEL 200WF".

Powdered cellulose, trade name "VITACEL LOO" or "VITACEL L700G".

Oat fiber, trade name "VITACEL HF 600".

Pea fiber, trade name "VITACEL EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bamboo fibers, powdered cellulose, bran fibers, and cellulose fiber.

For example, a powdered flavor composition comprising menthol as the flavor compound may be used as the powdered flavor composition, whereas e.g. a liquid flavor composition comprising peppermint as the flavor compound may be used as the liquid flavor composition. Of course, other flavors as described herein may be use as well, in combination with menthol and/or peppermint or replacing these. The amount of liquid and optionally powdered flavor composition may be adjusted in view of potency of the applied flavor, the concentration/loading of the flavor compound and the desired flavor strength.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC81-PPC92 shows the use of different fibers, in different amounts and with different nicotine premixes.

Pouches PPC93-PPC94 show use of buffer pair and higher amount of salt, respectively.

Example 4K—Pouches

Pouches PPC101-PPC103 containing nicotine premix are prepared comprising powdered compositions as outlined in table 18C. The pouches are made as follows.

Powdered ingredients including powdered flavor (if any) are mixed using a planetary BEAR VARIMIXER mixer for 2 minutes. Then, the nicotine is added and mixed for 2 minutes. Then water is slowly added while the mixer is running, followed by addition of liquid flavor. Finally, silicon dioxide is added and the mixed for about 1 minute. The total mixing time is about 30 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention. The pouch material of example 1B may also be used.

The powder is filled into pouches and is maintained in the pouch by a sealing.

TABLE 18C

The nicotine premix II comprises 34.1 wt % water, thereby contributing to the total water content.

| PPC | PPC101 | PPC102 | PPC103 |
|---|---|---|---|
| Amount of nicotine | 9.6 mg | 9.6 mg | 9.6 mg |
| Water content [wt %] | 15 | 30 | 45 |
| Density (gram per Liter) | 256 | 303 | 578 |
| Hausner ratio | 1.25 | 1.22 | 1.11 |
| Raw material | Content in weight percent | | |
| Nicotine premix II | 14.6 | 14.6 | 14.6 |
| Sugar alcohol(s) | 12.3 | 12.3 | 12.3 |
| Purified water | 10 | 25 | 40 |
| Wheat fiber | 45 | 30 | 15 |
| Sodium alginate | 2.0 | 2.0 | 2.0 |
| Sodium carbonate | 4.0 | 4.0 | 4.0 |
| Flavor | 9.0 | 9.0 | 9.0 |
| High intensity sweetener | 1.0 | 1.0 | 1.0 |
| Potassium sorbate | 0.1 | 0.1 | 0.1 |
| Silicon dioxide | 2.0 | 2.0 | 2.0 |
| Total | 100 | 100 | 100 |

Pouch content: 500 mg total, i.e. nicotine concentration 19.2 mg/g.

The sugar alcohol(s) may be Xylitol e.g. trade name "XYLITAB 200" and/or Isomalt e.g. tradename "GALENIQ 720".

Wheat fiber, trade name "VITACEL 600 WF PLUS". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC101-PPC101 show pouches having different water and water-insoluble fiber contents.

Example 4L—Content Uniformity Measurements

Content Uniformity (CU) of a pouch sample was determined by analysis of 10 replicate sub-samples. For each sub-sample of approx. 500 mg, the content of nicotine was determined using standard HPLC techniques. The nicotine content of a sub-sample was expressed as a percentage relative to the nominal content of nicotine in the sample (i.e. % Label Claim). For example, a pouch sample with a nominal content of nicotine of 20 mg/g being analyzed to have an actual content of 19 mg/g would have a nicotine content of 95% Label Claim.

The Content Uniformity of the sample is then determined as the Relative Standard Deviation (RSD) of the individual analyses of relative nicotine content in the 10 replicates.

Homogeneity was evaluated on two batches of PPC46 produced differently. PPC46 was produced in accordance with claim 1, i.e. the liquid flavor was added after water, whereas PPC46* was produced similarly, however by adding the liquid flavor composition to the powdered composition, where after water was added. I.e. when making PPC46*, the liquid flavor composition is added before adding water.

PPC46* was visually found to be significantly less homogeneous than PPC46. This was confirmed by nicotine CU analysis, as can be observed from table 19 below. Moreover, the powder composition of PPC46* contained lumps of varying sizes, visually confirming the inhomogeneous distribution. The relative standard deviation was measured, confirming that PPC46* was less homogenous than PPC46.

Both pouch compositions were sieved through a 1400-micron sieve, where after RSD of nicotine was measured again. Again PPC46* was found to be less homogeneous than PPC46.

TABLE 19

| PPC | RSD |
|---|---|
| PPC46-sieved | 0.9 |
| PPC46*-sieved | 1.7 |
| PPC46-un-sieved | 2.5 |
| PPC46*-un-sieved | 4.7 |

Example 5—Evaluation

The produced pouches of the invention were evaluated and found to have a very attractive flavor release. This was verified for pouches with and without nicotine.

The pouched products PPC1 and PNN1 were compared to the Comp. P1 and P2 pouch with respect to perceived flavor release.

Evaluation of perceived flavor release is performed as described in the following.

Perceived flavor release was evaluated by a test panel of 4 trained assessors. Each assessor evaluates all samples twice. Average evaluations are estimated.

The pouched products PNN1 and PPC1 were evaluated to have a significant faster onset of flavor release and a significant initial flavor burst by all four assessors, when comparing to the Comp. P1-P2.

The pouch product PPC1 was evaluated with respect to perceived effect from nicotine and with respect to burning (tingling) sensation.

Evaluation of perceived effect from nicotine and burning (tingling) sensation is performed as described in the following.

Perceived effect from nicotine and burning (tingling) sensation was evaluated by a test panel of 4 trained assessors. Each assessor evaluates all samples twice. Average evaluations are estimated.

The pouch product PPC1 was evaluated to have a fast onset of action and a high perceived effect from nicotine by all four assessors. Also, all four assessors evaluated the pouch product PPC1 to have a high burning (tingling) sensation.

Similarly, the pouch product PPC1 was evaluated with respect to perceived effect from nicotine in the same way as described above. The pouch product PPC1 was evaluated to have a high perceived effect from nicotine by all four assessors.

Further, the flavor burst was evaluated to be desirable in combination to burning (tingling) sensation.

Example 6—User Evaluations

Pouches PNN30 and Comp.P1 were made according to example 2C. COMP.P1 was made with 8 wt % blackcurrant powdered flavor and no liquid flavor. PNN30 was made with 5 wt % blackcurrant powdered flavor and 1.5 wt % blackcurrant liquid flavor.

The amount of liquid and optionally powdered flavor composition is adjusted in view of potency of the applied flavor, the concentration/loading of the flavor compound and the desired flavor strength.

Pouches PPC28 and COMP.P2 were made according to example 4A.

The pouches were evaluated by a test-panel of 4 trained assessors. Each assessor evaluated all samples twice. The test-panel evaluated the pouches on 4 different parameters over 30 min: moisture sensation, flavor intensity, sweetness intensity and overall taste intensity.

TABLE 20

| Minutes | Overall taste intensity | | Sweetness intensity | | Flavor intensity | | Moisture sensation | |
|---|---|---|---|---|---|---|---|---|
| | PNN 30 | Comp. P1 | PNN 30 | Comp. P1 | PNN 30 | Comp. P1 | PNN 30 | Comp. P1 |
| 1 | 2 | 1 | 1 | 1 | 2 | 1 | 2 | 1 |
| 2 | 2 | 1.5 | 2 | 1 | 3 | 1.5 | 3 | 1.5 |
| 3 | 3 | 2 | 3 | 1 | 3 | 2 | 3 | 2 |
| 4 | 3 | 3 | 4 | 2 | 3 | 2 | 4 | 2 |
| 5 | 3 | 3 | 4 | 3 | 3 | 3 | 4 | 3 |
| 6 | 3 | 3 | 4 | 3 | 3 | 3 | 4 | 3 |
| 7 | 3 | 3 | 4 | 3 | 4 | 3 | 4 | 3 |
| 8 | 3 | 3 | 4 | 3 | 4 | 3 | 4 | 3 |
| 9 | 3 | 3 | 4 | 3 | 4 | 3 | 4 | 3 |
| 10 | 3 | 3 | 4 | 3 | 4 | 3.5 | 4 | 3 |
| 11 | 3 | 3 | 4 | 3 | 4 | 4 | 4 | 3 |
| 12 | 3 | 3 | 4 | 3 | 4 | 4 | 4 | 3 |
| 13 | 3 | 3 | 4 | 3 | 4 | 4 | 4 | 3 |
| 14 | 3 | 3 | 4 | 3 | 4 | 4 | 4 | 3 |
| 15 | 3 | 3 | 4 | 3 | 4 | 4 | 4 | 3 |
| 20 | 3 | 3 | 4 | 3 | 4 | 3 | 4 | 3 |
| 25 | 3 | 3 | 4 | 3 | 4 | 3 | 4 | 3 |
| 30 | 3 | 3 | 4 | 2 | 4 | 2 | 4 | 2 |

Ratings:
1: Low
2: Below medium
3: Medium
4: Above medium
5: High.

The test panel found that pouches comprising liquid flavor compared to pouches without liquid flavor, scored higher on all parameters in the initial time of use, i.e. during the first 5 minutes.

PNN30 had an improved moisture sensation in the initial time of use.

PNN30 had a higher flavor intensity and sweetness intensity both in the initial time of use and throughout the use period, indicating that the pouches facilitate an initial fast release of flavor and sweetener, but also a sustained release during use.

The overall taste intensity was likewise found to be better for PNN30, both in the initial time of use and throughout the use period.

The above test was repeated for pouches PPC28 and COMP.P2, confirming the result that inclusion of liquid flavor provided a higher flavor intensity.

The invention claimed is:

1. An oral pouched product comprising:
   a saliva permeable pouch; and
   a non-tobacco pouch composition; wherein,
   the non-tobacco pouch composition comprises:
   a powdered composition,
   and
   a liquid flavor composition adsorbed to a surface of the powdered composition in an amount of 0.5-3% by weight of the pouch composition,
   wherein the powdered composition comprises:
   a water-insoluble fiber,
   at least one sugar alcohol in an amount of 5-70% by weight of the pouch composition,
   a powdered flavor composition in an amount of 5-20% by weight of the pouch composition, and
   water,
   wherein the powdered flavor composition comprises a flavor compound immobilized to a powdered carrier or within a powdered carrier, or the powdered flavor composition comprises an essential oil added to a powdered carrier, and
   wherein a total amount of the liquid flavor composition and the powdered flavor composition is no more than 10% by weight of the pouch composition.

2. The oral pouched product according to claim 1, wherein the pouch composition comprises the powdered flavor composition in an amount of 5-10% by weight of the pouch composition.

3. The oral pouched product according to claim 1, wherein the powdered flavor composition provides flavor compound or essential oil in an amount of 0.1% to 9% by weight of the pouch composition.

4. The oral pouched product according to claim 1, wherein the at least one sugar alcohol is selected from the group consisting of xylitol, mannitol, erythritol, isomalt, sorbitol, lactitol, and mixtures thereof, and wherein the pouch composition comprises the at least one sugar alcohol in an amount of 10 to 70% by weight of the pouch composition.

5. The oral pouched product according to claim 1, wherein the water-insoluble fiber is a plant fiber selected from the group consisting of wheat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, cellulose fibers, bran fibers, bamboo fibers, powdered cellulose, and any combination thereof.

6. The oral pouched product according to claim 1, wherein the pouch composition comprises water in an amount of 20-65% by weight of the pouch composition.

7. The oral pouched product according to claim 1, wherein the pouch composition further comprises nicotine in an amount of at least 0.1% by weight.

8. The oral pouched product according to claim 7, the nicotine comprises non-salt nicotine.

9. The oral pouched product according to claim 7, wherein the nicotine comprises nicotine free base.

10. The oral pouched product according to claim 7, wherein the nicotine comprises nicotine mixed with ion exchange resin.

11. The oral pouched product according claim 1, wherein the pouch composition comprises a pH-regulating agent in an amount of less than 5% by weight of the pouch composition.

12. The oral pouched product according to claim 1, wherein the pouch composition comprises nicotine in an amount of at least 0.2% by weight of the pouch composition.

13. A method of manufacturing an oral non-tobacco pouched product, the method comprising:
    providing a powdered composition, comprising:
    a water-insoluble fiber,
    at least one sugar alcohol in an amount of 5-70% by weight of the oral non-tobacco pouched product, and
    a powdered flavor composition in an amount of 5-20% by weight of the oral non-tobacco pouched product,
    mixing water with said powdered composition to obtain a mixture,
    adding from 0.5-3% by weight of the oral non-tobacco pouched product of a liquid flavor composition to the mixture of the water and the powdered composition to adsorb the liquid flavor composition to a surface of the powdered composition to obtain the oral non-tobacco pouched product, and
    adding the oral non-tobacco pouched product to a saliva-permeable pouch,
    wherein the powdered flavor composition comprises a flavor compound immobilized to a powdered carrier or within a powdered carrier, or the powdered flavor composition comprises an essential oil added to a powdered carrier, and
    wherein a total amount of the liquid flavor composition and the powdered flavor composition is no more than 10 by weight of the oral non-tobacco pouched product.

14. The method according to claim 13, wherein nicotine is added to the mixture of the water and the powdered composition before adding the liquid flavor composition.

* * * * *